(12) United States Patent
Harlacher et al.

(10) Patent No.: US 12,187,703 B2
(45) Date of Patent: Jan. 7, 2025

(54) CRYSTALLINE FORMS OF N-(3-(2-(2-HYDROXYETHOXY)-6-MORPHOLINOPYRIDIN-4-YL)-4-METHYLPHENYL)-2(TRIFLUOROMETHYL)ISONICOTINAMIDE AS RAF INHIBITORS FOR THE TREATMENT OF CANCER

(71) Applicant: NOVARTIS AG, Basel (CH)

(72) Inventors: Cornelius Stephen Harlacher, Reinach (CH); Zaixing Li, Shanghai (CN); Liladhar Murlidhar Waykole, Succasunna, NJ (US)

(73) Assignee: NOVARTIS AG, Basel (CH)

( * ) Notice: Subject to any disclaimer, the term of this patent is extended or adjusted under 35 U.S.C. 154(b) by 602 days.

(21) Appl. No.: 17/610,321

(22) PCT Filed: May 12, 2020

(86) PCT No.: PCT/IB2020/054491
§ 371 (c)(1),
(2) Date: Nov. 10, 2021

(87) PCT Pub. No.: WO2020/230028
PCT Pub. Date: Nov. 19, 2020

(65) Prior Publication Data
US 2022/0267299 A1    Aug. 25, 2022

(30) Foreign Application Priority Data

May 13, 2019    (WO) ................ PCT/CN2019/086595

(51) Int. Cl.
C07D 401/12    (2006.01)
(52) U.S. Cl.
CPC ........ *C07D 401/12* (2013.01); *C07B 2200/13* (2013.01)
(58) Field of Classification Search
CPC ............. C07B 2200/13; C07D 401/12; C07D 413/14; A61K 31/5377; A61P 35/00
See application file for complete search history.

(56) References Cited

U.S. PATENT DOCUMENTS

| | | | |
|---|---|---|---|
| 3,707,475 A | 12/1972 | Joseph | |
| 5,717,100 A | 2/1998 | Selnick et al. | |
| 6,211,177 B1 | 4/2001 | Sperl et al. | |
| 6,248,771 B1 | 6/2001 | Shenoy et al. | |
| 6,268,391 B1 | 7/2001 | Dickerson et al. | |
| 6,358,932 B1 | 3/2002 | Monia | |
| 6,399,603 B1 | 6/2002 | Jacobs et al. | |
| 6,417,194 B1 | 7/2002 | Fox et al. | |
| 6,458,813 B1 | 10/2002 | Mantlo et al. | |
| 6,465,493 B1 | 10/2002 | Burgess et al. | |
| 6,608,053 B2 | 8/2003 | Hayakawa et al. | |
| 7,071,216 B2 | 7/2006 | Renhowe et al. | |
| 7,423,150 B2 | 9/2008 | Costales et al. | |
| 7,531,553 B2 | 5/2009 | Di et al. | |
| 8,129,394 B2 | 3/2012 | Hunag et al. | |
| 8,242,260 B2 | 8/2012 | Costales et al. | |
| 8,299,108 B2 | 10/2012 | Amiri et al. | |
| 8,415,382 B2 | 4/2013 | Costales et al. | |
| 8,563,553 B2 | 10/2013 | Costales et al. | |
| 9,242,969 B2 | 1/2016 | Barsanti et al. | |
| 9,474,754 B2 | 10/2016 | Caponigro et al. | |
| 9,694,016 B2 | 7/2017 | Aversa et al. | |
| 9,700,557 B2 | 7/2017 | Caponigro et al. | |
| 9,867,825 B2 | 1/2018 | Caponigro et al. | |
| 9,913,844 B2 | 3/2018 | Caponigro et al. | |
| 10,245,267 B2 | 4/2019 | Aversa et al. | |
| 10,328,066 B2 | 6/2019 | Caponigro et al. | |
| 10,485,788 B2 | 11/2019 | Caponigro et al. | |
| 10,548,894 B2 | 2/2020 | Caponigro et al. | |
| 10,709,712 B2 | 7/2020 | Aversa et al. | |
| 10,973,829 B2 | 4/2021 | Caponigro et al. | |
| 11,266,653 B2 | 3/2022 | Cooke | |
| 12,011,449 B2 | 6/2024 | Caponigro et al. | |
| 12,036,227 B2 | 7/2024 | Cooke | |
| 2001/0014679 A1 | 8/2001 | Tang et al. | |
| 2002/0151544 A1 | 10/2002 | Hayakawa et al. | |
| 2003/0166633 A1 | 9/2003 | Gaster et al. | |
| 2004/0053973 A1 | 3/2004 | Ohkawa et al. | |

(Continued)

FOREIGN PATENT DOCUMENTS

| | | |
|---|---|---|
| DE | 2155558 A1 | 6/1972 |
| DE | 3029376 A1 | 3/1982 |

(Continued)

OTHER PUBLICATIONS

Alali et al. Chemical interrogation of the neuronal kinome using a primary cellbased screening assay. ACS Chem Biol. 8(5):1027 (2013).

Andreyev et al. Kirsten ras mutations in patients with colorectal cancer: the multicenter "Rascal" study. J Natl Cancer Inst. 90(9):675 (1998).

Anonymous. History of Changes for Study: NCT02974725 A Phase Ib Study of LXH254-centric Combinations in NSCLC or Melanoma. ClinicalTrials.gov archive Retrieved from the Internet: URL:https://www.clinicaltrials.gov/ct2/history/NCT02974725?V13=View#StudyPageTop [retrieved on Mar. 12, 2020] (Jan. 17, 2019).

(Continued)

*Primary Examiner* — Jean P Cornet
(74) *Attorney, Agent, or Firm* — WILSON SONSINI GOODRICH & ROSATI

(57) ABSTRACT

The present invention relates to crystalline forms of N-(3-(2-(2-hydroxyethoxy)-6-morpholinopyridin-4-yl)-4-methylphenyl)-2-(trifluoromethyl)isonicotinanmide and to processes for their preparation. Furthermore, the invention relates to a pharmaceutical composition comprising said crystalline forms of N-(3-(2-(2-hydroxyethoxy)-6-morpholinopyridin-4-yl)-4-methylphenyl)-2-trifluoromethyl) isonicotinamide, and at least one pharmaceutically acceptable excipient. The pharmaceutical composition of the present invention can be used as a medicament, in particular for the treatment of cancers.

16 Claims, 9 Drawing Sheets

(56) References Cited

U.S. PATENT DOCUMENTS

| | | |
|---|---|---|
| 2004/0063946 A1 | 4/2004 | Ohkawa et al. |
| 2004/0087626 A1 | 5/2004 | Renhowe et al. |
| 2004/0122237 A1 | 6/2004 | Amiri et al. |
| 2005/0192287 A1 | 9/2005 | Costales et al. |
| 2005/0282805 A1 | 12/2005 | Hangeland et al. |
| 2008/0051401 A1 | 2/2008 | Pass |
| 2009/0005359 A1 | 1/2009 | Cossrow et al. |
| 2009/0298815 A1 | 12/2009 | Adams et al. |
| 2010/0069629 A1 | 3/2010 | Shimma et al. |
| 2013/0096149 A1 | 4/2013 | Madera et al. |
| 2013/0165456 A1 | 6/2013 | Gilmer et al. |
| 2013/0210818 A1 | 8/2013 | Huang et al. |
| 2013/0217698 A1 | 8/2013 | Calienni et al. |
| 2013/0224195 A1 | 8/2013 | Costales et al. |
| 2014/0011825 A1 | 1/2014 | Costales et al. |
| 2014/0178360 A1 | 6/2014 | Kuo et al. |
| 2014/0275003 A1 | 9/2014 | Barsanti et al. |
| 2015/0126490 A1 | 5/2015 | Bagdanoff et al. |
| 2015/0216868 A1 | 8/2015 | Laquerre et al. |
| 2016/0038504 A1 | 2/2016 | Aversa et al. |
| 2016/0075727 A1 | 3/2016 | Burger et al. |
| 2017/0202842 A1 | 7/2017 | Laquerre et al. |
| 2017/0260207 A1 | 9/2017 | Aversa et al. |
| 2018/0127412 A1 | 5/2018 | Zhang et al. |
| 2019/0022243 A1 | 1/2019 | Boshuizen et al. |
| 2022/0008426 A1 | 1/2022 | Caponigro et al. |
| 2022/0143036 A1 | 5/2022 | Cooke |
| 2023/0226030 A1 | 7/2023 | Caponigro et al. |
| 2023/0321110 A1 | 10/2023 | Caponigro et al. |
| 2024/0000789 A1 | 1/2024 | Caponigro et al. |

FOREIGN PATENT DOCUMENTS

| | | | |
|---|---|---|---|
| EP | 0149884 B1 | 12/1992 | |
| EP | 1232153 B1 | 11/2004 | |
| EP | 1721905 A1 | 11/2006 | |
| GB | 2306108 A | 4/1997 | |
| JP | H02188579 A | 7/1990 | |
| JP | H03157383 A | 7/1991 | |
| JP | 2000302680 A | 10/2000 | |
| JP | 2007246520 A | 9/2007 | |
| WO | WO-9808845 A1 | 3/1998 | |
| WO | WO-0042012 A1 | 7/2000 | |
| WO | WO-0059506 A1 | 10/2000 | |
| WO | WO-0062778 A1 | 10/2000 | |
| WO | WO-0138324 A2 | 5/2001 | |
| WO | WO-0152845 A1 | 7/2001 | |
| WO | WO-0152846 A1 | 7/2001 | |
| WO | WO-0162756 A1 | 8/2001 | |
| WO | WO-0166539 A1 | 9/2001 | |
| WO | WO-0166540 A1 | 9/2001 | |
| WO | WO-0172737 A1 | 10/2001 | |
| WO | WO-0196308 A1 | 12/2001 | |
| WO | WO-0206213 A2 | 1/2002 | |
| WO | WO-0239954 A2 | 5/2002 | |
| WO | WO-0242273 A2 | 5/2002 | |
| WO | WO-0244156 A2 | 6/2002 | |
| WO | WO-02064136 A2 | 8/2002 | |
| WO | WO-02076960 A1 | 10/2002 | |
| WO | WO-02094808 A1 | 11/2002 | |
| WO | WO-03047577 A2 | 6/2003 | |
| WO | WO-03082272 A1 | 10/2003 | |
| WO | WO-03087304 A2 | 10/2003 | |
| WO | WO-2004002948 A1 | 1/2004 | |
| WO | WO-2004016791 A2 | 2/2004 | |
| WO | WO-2004026859 A1 | 4/2004 | |
| WO | WO-2004026863 A1 | 4/2004 | |
| WO | WO-2004085425 A1 | 10/2004 | |
| WO | WO-2005028444 A1 | 3/2005 | |
| WO | WO-2005034869 A2 | 4/2005 | |
| WO | WO-2005047266 A1 | 5/2005 | |
| WO | WO-2005103028 A1 | 11/2005 | |
| WO | WO-2005105814 A1 | 11/2005 | |
| WO | WO-2005116000 A1 | 12/2005 | |
| WO | WO-2005121142 A1 | 12/2005 | |
| WO | WO-2005123050 A2 | 12/2005 | |
| WO | WO-2006005914 A1 | 1/2006 | |
| WO | WO-2006005915 A1 | 1/2006 | |
| WO | WO-2006005918 A1 | 1/2006 | |
| WO | WO-2006026306 A1 | 3/2006 | |
| WO | WO-2006038734 A1 | 4/2006 | |
| WO | WO-2006044509 A2 | 4/2006 | |
| WO | WO-2007118149 A2 | 10/2007 | |
| WO | WO-2008018426 A1 | 2/2008 | |
| WO | WO-2008071605 A2 | 6/2008 | |
| WO | WO-2009001132 A1 | 12/2008 | |
| WO | WO-2009003998 A2 | 1/2009 | |
| WO | WO-2009006389 A2 | 1/2009 | |
| WO | WO-2009007749 A2 | 1/2009 | |
| WO | WO-2009012283 A1 | 1/2009 | |
| WO | WO-2009014637 A2 | 1/2009 | |
| WO | WO-2009030952 A2 | 3/2009 | |
| WO | WO-2009032667 A1 | 3/2009 | |
| WO | WO-2009047163 A1 | 4/2009 | |
| WO | WO-2009106885 A1 | 9/2009 | |
| WO | WO-2009115572 A2 | 9/2009 | |
| WO | WO-2009137391 A2 | 11/2009 | |
| WO | WO-2009152356 A2 | 12/2009 | |
| WO | WO-2010010154 A1 | 1/2010 | |
| WO | WO-2010020675 A1 | 2/2010 | |
| WO | WO-2010048149 A2 | 4/2010 | |
| WO | WO-2010071837 A1 | 6/2010 | |
| WO | WO-2011026911 A1 | 3/2011 | |
| WO | WO-2011059610 A1 | 5/2011 | |
| WO | WO-2011081205 A1 | 7/2011 | |
| WO | WO-2011139107 A2 | 11/2011 | |
| WO | WO-2012034363 A1 | 3/2012 | |
| WO | WO-2012088033 A2 | 6/2012 | |
| WO | WO-2012109075 A1 | 8/2012 | |
| WO | WO-2012125981 A2 | 9/2012 | |
| WO | WO-2013022766 A1 | 2/2013 | |
| WO | WO-2013033167 A1 | 3/2013 | |
| WO | WO-2013041652 A1 | 3/2013 | |
| WO | WO-2013164769 A1 | 11/2013 | |
| WO | WO-2013171640 A1 | 11/2013 | |
| WO | WO-2014008214 A1 | 1/2014 | |
| WO | WO-2014018725 A1 | 1/2014 | |
| WO | WO-2014039375 A1 | 3/2014 | |
| WO | WO-2014052699 A1 | 4/2014 | |
| WO | WO-2014058691 A1 | 4/2014 | |
| WO | WO-2014151616 A1 * | 9/2014 | ........... A61K 31/444 |
| WO | WO-2015066188 A1 | 5/2015 | |
| WO | WO-2015095819 A2 | 6/2015 | |
| WO | WO-2016038581 A1 | 3/2016 | |
| WO | WO-2016038582 A1 | 3/2016 | |
| WO | WO-2016038583 A1 | 3/2016 | |
| WO | WO-2016115376 A1 | 7/2016 | |
| WO | WO-2017037587 A1 | 3/2017 | |
| WO | WO-2017212442 A1 | 12/2017 | |
| WO | WO-2018051306 A1 | 3/2018 | |
| WO | WO-2018107146 A1 | 6/2018 | |
| WO | WO-2018203219 A1 | 11/2018 | |
| WO | WO-2018213302 A1 | 11/2018 | |
| WO | WO-2019051296 A1 | 3/2019 | |
| WO | WO-2020046966 A1 | 3/2020 | |
| WO | WO-2020128878 A1 | 6/2020 | |
| WO | WO-2020230028 A1 | 11/2020 | |
| WO | WO-2021165849 A1 | 8/2021 | |
| WO | WO-2021229439 A1 | 11/2021 | |
| WO | WO-2022043955 A1 | 3/2022 | |

OTHER PUBLICATIONS

Atefi et al. Combination of pan-RAF and MEK inhibitors in NRAS mutant melanoma. Mol Cancer 14(1):27 (2015).

Babchia et al. The P13K/Akt and mTOR/P70S6K signaling pathways in human uveal melanoma cells: interaction with BRaf/ERK. Invest Ophthalmol Vis Sci. 51(1):421 (2010).

Banker Modern Pharmaceutics. Marcel Dekker. New York. (1996) 3 pages.

Belikov. Pharmaceutical Chemistry: Manual. Moscow: MEDpress-inform (pp. 27-29) (2007).

(56) References Cited

OTHER PUBLICATIONS

Blasco et al. c-Raf but not B-Raf, is essential for development of K-Ras oncogene-driven non-small cell lung carcinoma. Cancer Cell 19(5):652-63 (2011).
Bos. Ras oncogenes in human cancer: a review. Cancer Res. 49(17):4682 (1989).
Brose et al. BRAF and RAS Mutations in Human Lung Cancer and Melanoma. Cancer Research 62(23):6997-7000 (Dec. 1, 2002).
Cantwell-Dorris et al. BRAFV600E: implications for carcinogenesis and molecular therapy. Mol Cancer Ther. Mar. 10(3):385-94 (2011).
CAS Registry No. 730972-83-5, STN Entry Date Aug. 23, 2004.
CAS Registry No. 867157-50-4, STN Entry Date Nov. 10, 2005.
Cox et al. Drugging the undruggable RAS: Mission possible? Nat Rev Drug Discov 13:828-851 (2014).
Dagogo-Jack et al. Impact of BRAF Mutation Class on Disease Characteristics and Clinical Outcomes in BRAF-mutant Lung Cancer. Clin Cancer Res 25(1):158-165 (2019).
Dankner et al., Classifying BRAF alterations in cancer: new rational therapeutic strategies for actionable mutations. Oncogene 37(24):3183-3199 (2018).
Davies et al. Mutations of the BRAF Gene in Human Cancer. Nature 417:949-954 (2002).
De Bono et al. Therapeutics targeting signal transduction for patients with colorectal carcinoma. Br Med Bull. 64:227-254 (2002).
Deng et al., Knowledge-based design of target-focused libraries using protein-ligand interaction constraints. J Med Chem. 49(2):490-500 (2006).
Di Magliano et al. Roles for KRAS in pancreatic tumor development and progression. Gastroenterology 144(6):1220-29 (2013).
Dummer et al., Binimetinib versus dacarbazine in patients with advanced NRAS-mutant melanoma (NEMO): a multicentre, open-label, randomised, phase 3 trial. Lancet Oncol 18:435-445 (2017).
Eisenhauer et al. New response evaluation criteria in solid tumours: revised Recist guideline (version 1.1). Euro J Cancer 45:228-247 (2009).
Fedorenko et al. Beyond BRAF: where next for melanoma therapy? British I Cancer 112:217-26 (2015).
Gao et al., Integrative analysis of complex cancer genomics and clinical profiles using the cBioPortal. Science signaling 6(269):pi1 (2013).
Golub et al., Molecular classification of cancer: class discovery and class prediction by gene expression monitoring. Science. 286(5439):531-537 (1999).
Gopalsamy et al. Hit to lead optimization of pyrazolo[15a]pyrimidines as BRaf kinase inhibitors. Bioorg Med Chem Lett. 19(24):6890 (2009).
Gura. Cancer Models: Systems for identifying new drugs are often faulty. Science 278(5340):1041-42 (Nov. 1997).
Hatzivassiliou et al. RAF inhibitors prime wildtype RAF to activate the MAPK pathway and enhance growth. Nature. 464:4315 (2010) (Includes Methods page and Supplementary Information).
Heidorn et al. Kinase-Dead BRAF and Oncogenic RAS Cooperate to Drive Tumor Progression through CRAF. Cell 140(2):209-221 (2010).
Hoshino et al. Constitutive activation of the 41-/43-kDa mitogen-activated protein kinase signaling pathway in human tumors. Oncogene 18(3):813-22 (1999).
Jakob et al. NRAS mutation status is an independent prognostic factor in metastatic melanoma. Cancer 118(16):4014-4023 (2012).
Jensen. A note on the term "Chalcogen." J Chem Edu 74(9):1063-4 (1997).
Johnson et al. Relationships Between Drug Activity in NCI Preclinical in Vitro and in Vivo Models and Early Clinical Trials. Br J Cancer 84(10):1424-1431 (2001).
Kawasaki et al. The second messenger phosphatidylinositol5phosphate facilitates antiviral innate immune signaling. Cell Host & Microbe. 14(2):148-58 (2013).
Kharkevich D.A. Pharmacology. Textbook, 2010, 10th edition, pp. 72-82.

Khimicheskiy Entsiklopedicheskiy Slovar. Chemical Encyclopedic Dictionary, Moscow: Sovetskaya Entsiklopediya, 1983, pp. 130-131.
Kim et al., Synthesis and biological evaluation of 4(5)-(6-alkylpyridin-2-yl)imidazoles as transforming growth factor-beta type 1 receptor kinase inhibitors. Journal of Medicinal Chemistry 50:3143-3147 (2007).
Kim et al., Synthesis of heteroaryl substituted imidazole derivatives. Bull Korean Chem Soc. 21(3):345-7 (2000).
Knickelbein et al. Mutant KRAS as a critical determinant of the therapeutic response of colorectal cancer. Genes & Disease 2(1):4-12 (2015).
Krayushkin et al., Photochromic dihetarylethenes. 7. Synthesis of bis(thienylazoles), photochromic analogs of diarylethenes. Russian Chemical Bulletin. International Edition 50(1):116-21 (2001).
Lala et al. Role of nitric oxide in tumor progression: Lessons from experimental tumors. Cancer and Metastasis Reviews 17(1):91-106 (1998).
Lamba et al., RAF suppression synergizes with MEK inhibition in KRAS mutant cancer cells. Cell Rep 8(5):1475-83 (2014).
Lambert et al. Targeting the P13K and MAPK pathways to treat Kaposi's-sarcoma-associated herpes virus infection and pathogenesis. Expert Opin Ther Targets 11(5):589-99 (2007).
Lito et al. Disruption of CRAF Mediated MEK Activation Is Required for Effective MEK Inhibition in KRAS Mutant Tumors. Cancer Cell 25:697-710 (2014).
Martin et al. Inhibition of PIKfyve by YM201636 dysregulates autophagy and leads to apoptosis-independent neuronal cell death. PLoS One 8(3):114 (2013).
Moore et al. Abstract 1816: Phase I study of the raf1 kinase inhibitor BAY 439006 in patients with advanced refractory solid tumors. Proceedings of the American Society of Clinical Oncology. (2002) . . . http://www.asco.org/portal/site/ASCO/template.RAW/ menuitem.34d60f5624ba07fd506fe . . . Last accessed Dec. 3, 2008. 2 pages.
Nakayama et al. KRAS or BRAF mutation status is a useful predictor of sensitivity to MEK inhibition in ovarian cancer. British J. Cancer 99 (12):2020-28 (2008).
Negrao et al. Molecular Landscape of BRAF-Mutant NSCLC Reveals an Association Between Clonality and Driver Mutations and Identifies Targetable Non-V600 Driver Mutations. J Thorac Oncol 15(10):1611-1623 (Jun. 13, 2020).
Paik et al. Clinical characteristics of patients with lung adenocarcinomas harboring BRAF mutations. J Clin Oncol. 29(15):2046-51 (2011).
Pao et al. KRAS mutations and primary resistance of lung adenocarcinomas to gefitinib or erlotinib. PLoS Med. 2(1):e17 (Jan. 2005).
Patani et al. Bioisosterism: A Rational Approach in Drug Design. Chem. Rev. 96:3147-3176 (1996).
PCT/IB2017/055641 International Invitation to Pay Additional Fees dated Nov. 29, 2017.
PCT/IB2017/055641 International Search Report and Written Opinion dated Feb. 2, 2018.
PCT/IB2018/052989 International Search Report and Written Opinion dated Jul. 24, 2018.
PCT/IB2020/054491 International Search Report and Written Opinion dated Jul. 7, 2020.
PCT/IB2021/051336 International Search Report and Written Opinion dated May 27, 2021.
PCT/IB2021/054013 International Search Report and Written Opinion dated Oct. 19, 2021.
PCT/US2014/026107 International Search Report and Written Opinion dated May 27, 2014.
Pearce et al. Chapter 18: Failure modes in anticancer drug discovery and development, Cancer Drug Design and Discovery Edited by Stephen Neidle pp. 424-435 (2008).
Pollock et al. High frequency of BRAF mutations in nevi. Nat Genet. 33(1):1920 (2003).
Poulikakos et al. RAF inhibitors transactivate RAF dimers and ERK signaling in cells with wild-type BRAF. Nature 464(7287):427-430 (2010).
Ramurthy et al. Design and Discovery of N-(3-(2-(2-Hydroxyethoxy)-6-morpholinopyridin-4-yl)-4-methylphenyl)-2-

(56) References Cited

OTHER PUBLICATIONS (trifluoromethyl)isonicotinamide, a Selective, Efficacious, and Well-Tolerated RAF Inhibitor Targeting RAS Mutant Cancers: The Path to the Clinic. J Med Chem 63(5):2013-2027 (2020).
Revesz et al., SAR of 2,6-diamino-3,5-difluoropyridinyl substituted heterocycles as novel p38MAP kinase inhibitors. Bioorg Med Chem Lett. 12(16):2109-12 (2002).
Rowinsky et al. Ras protein farnesyltransferase: A strategic target for anticancer therapeutic development. J Clin Oncol. 17(11):3631 (1999).
Samylina et al., Biopharmaceutical aspects of pharmacopoeial substances. Farmatsiya 8:29-32 (2012).
Scharovsky et al. Inhibition of ras oncogene: a novel approach to antineoplastic therapy. J Biomed Sci. 7(4):292-8 (2000).
Sholl et al. Institutional implementation of clinical tumor profiling on an unselected cancer population. JCI Insight 1:e87062 (2016).
Simone. Oncology: Introduction, Cecil Textbook of Medicine, 20th Edition, vol. 1004-1010 (1996).
Sloot et al. Long-term effects of BRAF inhibitors in melanoma treatment: friend or foe? Expert Opin Pharmacother 15(5):589-592 (2014).
Spring et al. Targeting the cyclin D-cyclin-dependent kinase (CDK)4/6-retinoblastoma pathway with selective CDK 4/6 inhibitors in hormone receptor-positive breast cancer: rational, current status, and future directions HHS Public Access. Discov Med 21(113):65-74 (2016).
Strumberg et al. Abstract 121: Final results of a phase I pharmacokinetic and pharmacodynamic study of the raf kinase inhibitor BAY 439006 in patients with solid tumors. Proceedings of the American Society of Clinical Oncology. (2002). http://www.asco.oreportal/site/ASCO/template.RAW/menuitem.34d60f5624ba07fd506fe . . . Last accessed Dec. 3, 2008. 2 pages.
Therasse et al. New guidelines to evaluate the response to treatment in solid tumors: European Organization for Research and Treatment of Cancer, National Cancer Institute of the United States, National Cancer Institute of Canada. J Natl Cancer Inst 92:205-216 (2000).
Tsai, et al. Discovery of a selective inhibitor of oncogenic B-Raf kinase with potent antimelanoma activity. PNAS. 2008; 105(8):3041-3046.
U.S. Appl. No. 14/204,823 Office Action dated Jan. 8, 2015.
U.S. Appl. No. 14/204,823 Office Action dated Jun. 4, 2015.
U.S. Appl. No. 15/601,423 Office Action dated Apr. 4, 2018.
U.S. Appl. No. 16/274,165 Office Action dated Oct. 2, 2019.
U.S. Appl. No. 16/332,120 Office Action dated Apr. 30, 2020.
U.S. Appl. No. 16/610,482 Office Action dated Jan. 22, 2021.
Weekes et al., Abstract CT107: A Phase Ib study to evaluate the MEK inhibitor cobimetinib in combination with the ERK1/2 inhibitor GDC-0994 in patients with advanced solid tumors. AACR Annual Meeting 2017. Apr. 1-5, 2017.
Wenglowsky et al. Pyrazolopyridine inhibitors of BRafV600E. Part 4: Rational design and kinase selectivity profile of cell potent type II inhibitors. Bioorg Med Chem Lett. 22(19):6237-41 (2012).
White et al., Chemiluminescence in liquid solutions: The chemiluminescence of Iophine and its derivatives. Photochemistry and Photobiology 4:1129-55 (1965).
Whittaker et al., Combined Pan-RAF and MEK Inhibition Overcomes Multiple Resistance Mechanisms to Selective RAF Inhibitors. Mol Cancer Ther 14(12):2700-2711 (2015).
Wolf et al. 1387P: Phase Ib study of LXH254 + LTT462 in patients with KRAS- or BRAF-mutant NSCLC. Annals of Oncology 31(S4):S881-S882 (Sep. 1, 2020).
Wolff. Burger's Medicinal Chemistry and Drug Discovery. 5th Ed. Part 1, pp. 975-977 (1995).
Wolin et al., Dual binding site inhibitors of B-RAF kinase. Bioorg Med Chem Lett 18:2825-9 (2008).
Yuen et al. Similarity of the phenotypic patterns associated with BRAF and KRAS mutations in colorectal neoplasia. Cancer Res. 62(22):6451-6455 (2002).
Zeitouni et al. KRAS Mutant Pancreatic Cancer: No Lone Path to an Effective Treatment. Cancer (Basel) 8(4):45 (Apr. 2016).
Zhang et al., The genomic landscape of cutaneous melanoma. Pigment Cell Melanoma Res 29:266-283 (2016).
Zheng et al., Anchored multiplex PCR for targeted next-generation sequencing. Nat Med 20:1479-84 (2014).
Zuccotto et al. Through the "Gatekeeper Door": Exploring the active kinase conformation. J Med Chem. 53(7):2681-94 (2010).
Co-pending U.S. Appl. No. 17/998,391, inventors Caponigro; Giordano et al., filed on Nov. 10, 2022.
Egas-Bejar et al., Rhabdomyosarcoma in adolescent and young adult patients: current perspectives. Adolesc Health Med Ther 5:115-25 (2014).
Hettmer et al., Rhabdomyosarcoma: current challenges and their implications for developing therapies. Cold Spring Harb Perspect Med 4(11):a025650 (2014).
Hobbs et al. RAS isoforms and mutations in cancer at a glance. J Cell Sci 129(7):1287-1292 (2016).
Liu et al. BRAF mutation and its inhibitors in sarcoma treatment. Cancer Med 9(14):4881-4896 (2020).
PCT/IB2021/057904 International Search Report and Written Opinion dated Nov. 4, 2021.
Pokrovsky. Small Medical Encyclopedia 4:81-83 (1996).
Punyko et al., Long-term medical effects of childhood and adolescent rhabdomyosarcoma: a report from the childhood cancer survivor study. Pediat Blood Cancer 44(7):643-53 (2005).
Rassidakis et al. Trametinib and Dabrafenib in histiocytic sarcoma transdifferentiated from chronic lymphocytic leukemia with a K-RAS and a unique BRAF mutation. Ann Hemato 99(3):649-651 (2020).
Rhee et al. Update on pediatric rhabdomyosarcoma: A report from the APSA Cancer Committee. J Pediatr Surg 55(10):1987-1995 (2020).
Stuart et al. Abstract DDT01-04: Pharmacological profile and anti-tumor properties of LXH254, a highly selective RAF kinase inhibitor. Cancer Res 78(13_SUpp):DDT01-04 (2018).
U.S. Appl. No. 17/191,205 Office Action dated Nov. 7, 2023.
U.S. Appl. No. 17/584,901 Office Action dated Dec. 6, 2023.
Vengerovsky, A.I., Pharmaceutical incompatibility. Bulletin of Siberian Medicine, 3:12 pages, 2003. http.7/old.ssmu.ru/bull/03/3/1684.pdf.
Watanabe et al. V600E mutation is a potential therapeutic target for a small subset of synovial sarcoma. Mod Patho 33(9):1660-1668 (2020).
Winette et al., Soft tissue sarcomas in adolescents and young adults: a comparison with their paediatric and adult counterparts. Lancet Oncol 18(3):e166-e175 (2017).
Ashizawa. Optimization of salts/crystal form and crystallization technique. Pharm Tech Japan 18(10):81-96 (2002).
Handbook of organic compound crystal preparation. Maruzen Co., Ltd.), Edited by Noriaki Hirayama. pp. 17-23, 37-40, 45-51, 57-65 (2008).
Dhillon. Dabrafenib plus Trametinib: a Review in Advanced Melanoma with a BRAFv600 Mutation. Target Oncol 11(3):417-428 (2016).
EP18726224.1 Communication of a Notice of Opposition dated Jan. 9, 2024.
McArthur. Combination Therapies to Inhibit the RAF/MEK/ERK Pathway in Melanoma: We are not Done Yet. Front Oncol 5:161 (2015).
Planchard et al. An open-label phase II trial of dabrafenib (D) in combination with trametinib (T) in patients (pts) with previously treated BRAF V600E-mutant advanced non-small cell lung cancer (NSCLC; BRF113928). J Clin Oncol 34(15):107 (2016) (Abstract).
Tran et al. MEK inhibitors and their potential in the treatment of advanced melanoma: the advantages of combination therapy. Drug Des Devel Ther 10:43-52 (2015).
Byrn et al. Pharmaceutical Solids: A Strategic Approach to Regulatory Considerations. Pharmaceutical Research 12(7):945-954 (1995).
Caira, Mino R., Crystalline Polymorphism of Organic Compounds. Topics in Current Chemistry 198:163-208 (1998).
Sarma, Bipul et al. Solid forms of pharmaceuticals: Polymorphs, salts and cocrystals. Korean Journal of Chemical Engineering 28:315-322 (2011).
Tian, Fang, et al. Factors affecting crystallization of hydrates. Journal of Pharmacy and Pharmacology 62(11):1534-1546 (2010).

(56) References Cited

OTHER PUBLICATIONS

Variankaval, Narayan, et al., From form to function: Crystallization of active pharmaceutical ingredients. AIChE Journal 54(7):1682-1688 (2008).

Augsburger, Larry L., et al. Pharmaceutical Dosage Forms: Tablets. Informa Healthcare, 3rd Edition, 2:62-66 (2008).

Braga et al., Crystal Polymorphism and Multiple Crystal Forms. Structure and Bonding 132:25-50 (2009).

Brittain et al. Chapter 1 & 5: Polymorphism in pharmaceutical solids. Edited by H. G. Brittain, Marcel Dekker, D.J.W. Grant (chapter 1—p. 1-10) and J. K. Guillory (Chapter 5—pp. 183-226) (Dec. 31, 1999).

Co-pending U.S. Appl. No. 18/679,016, inventor Cooke; Vesselina, filed on May 30, 2024.

Corcoran, et al. Combined BRAF and MEK Inhibition With Dabrafenib and Trametinib in BRAF V600-Mutant Colorectal Cancer. J Clin Oncol. 33(34):4023-4031 (2015).

De Braud, Filippo et al. Initial Evidence for the Efficacy of Naporafenib in Combination With Trametinib in NRAS-Mutant Melanoma: Results From the Expansion Arm of a Phase Ib, Open-Label Study. J Clin Oncol 41(14):2651-2660 (2023).

Henry et al. Discovery of 1-(3,3-dimethylbutyl)-3-(2-fluoro-4-methyl-5-(7-methyl-2-(methylamino)pyrido[2,3-d]pyrimidin-6-yl)phenyl)urea (LY3009120) as a pan-RAF inhibitor with minimal paradoxical activation and activity against BRAF or RAS mutant tumor cells. J Med Chem 58:4165-4179 (2015).

Hilfiker, Rolf. Relevance of Solid-State Properties for Pharmaceutical Products. Polymorphism: in the Pharmaceutical Industry (pp. 1-19) (2006).

Kopetz, et al. Encorafenib, Binimetinib, and Cetuximab in BRAF V600E-Mutated Colorectal Cancer. N Engl J Med. 381(17):1632-1643 (2019).

Kopetz, Scott et al. Phase II Pilot Study of Vemurafenib in Patients With Metastatic BRAF-Mutated Colorectal Cancer. J Clin Oncol 33(34):4032-4038 (2015).

Mandal et al. Stamping out RAF and MEK1/2 to inhibit the ERK1/2 pathway: an emerging threat to anticancer therapy. Oncogene 35(20):2547-61 (2016).

Peng et al., Inhibition of RAF Isoforms and Active Dimers by LY3009120 Leads to Anti-tumor Activities in RAS or BRAF Mutant Cancers. Cancer Cell 28(3):384-98 (2015).

Yadav et al. Co-targeting BRAF and cyclin dependent kinases 4/6 for BRAF mutant cancers. Pharmacol Ther 149:139-49 (2015).

\* cited by examiner

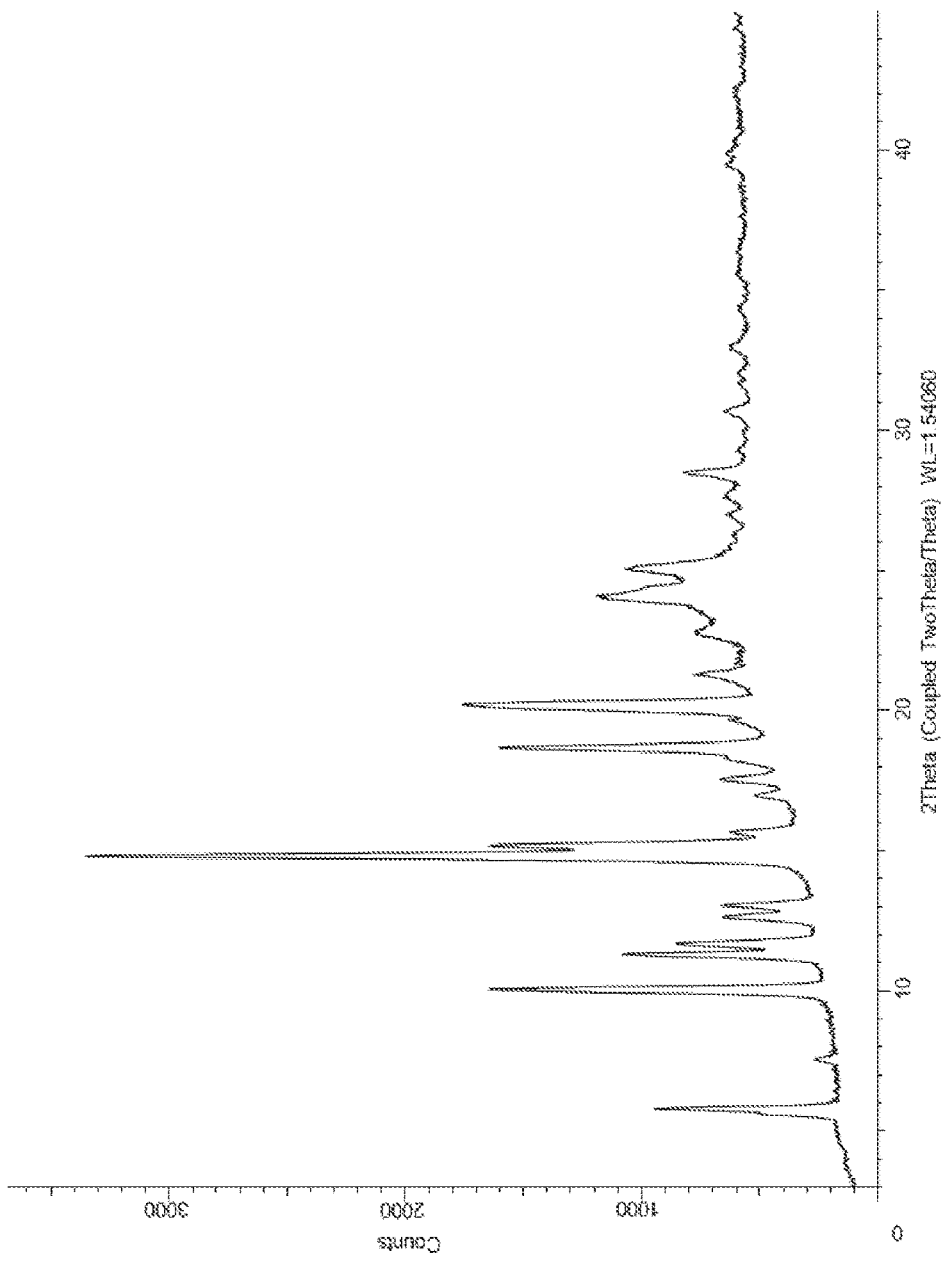
Figure 1. X-ray powder diffraction spectrum of crystalline Form A

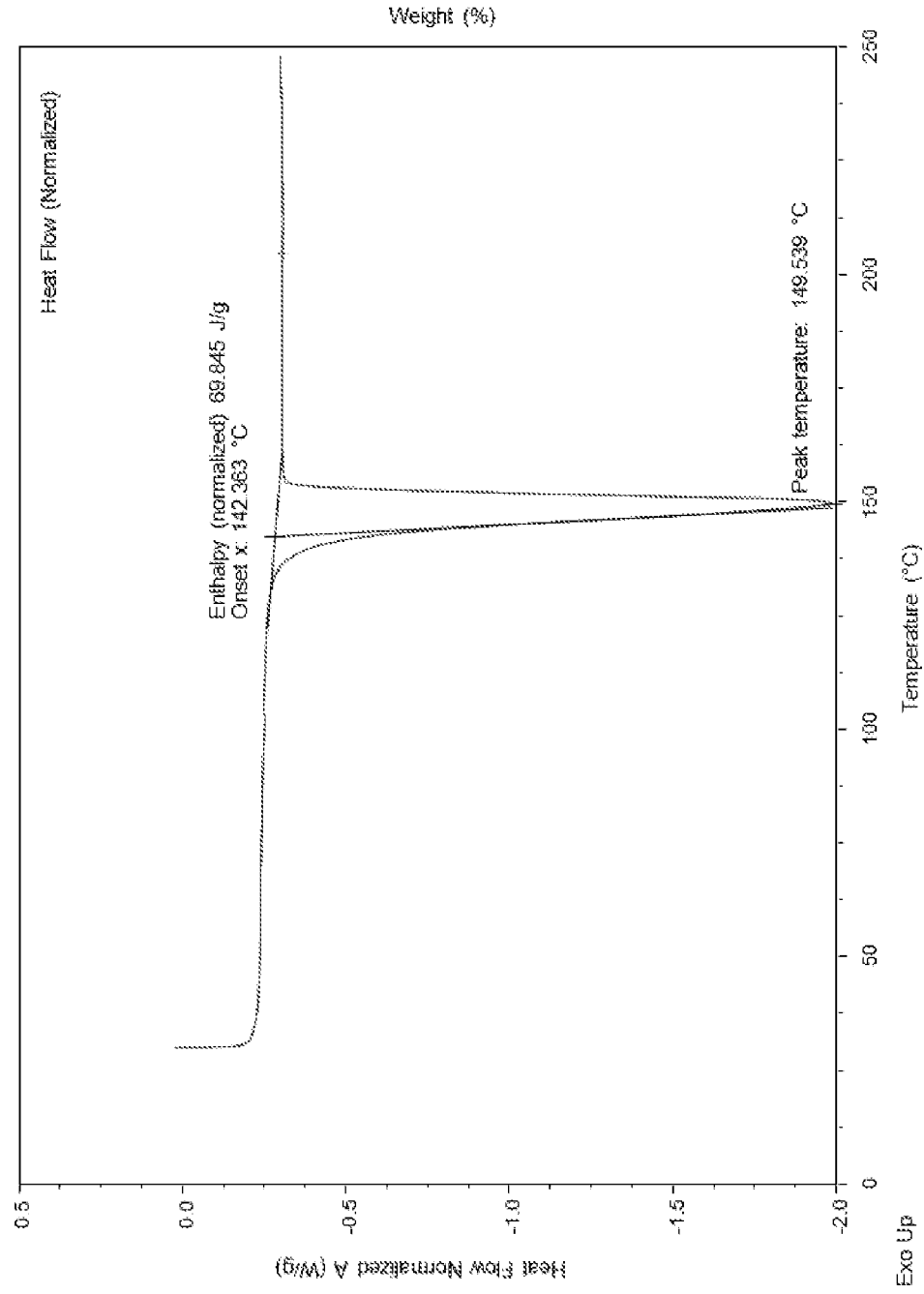
Figure 2. DSC thermogram of crystalline Form A

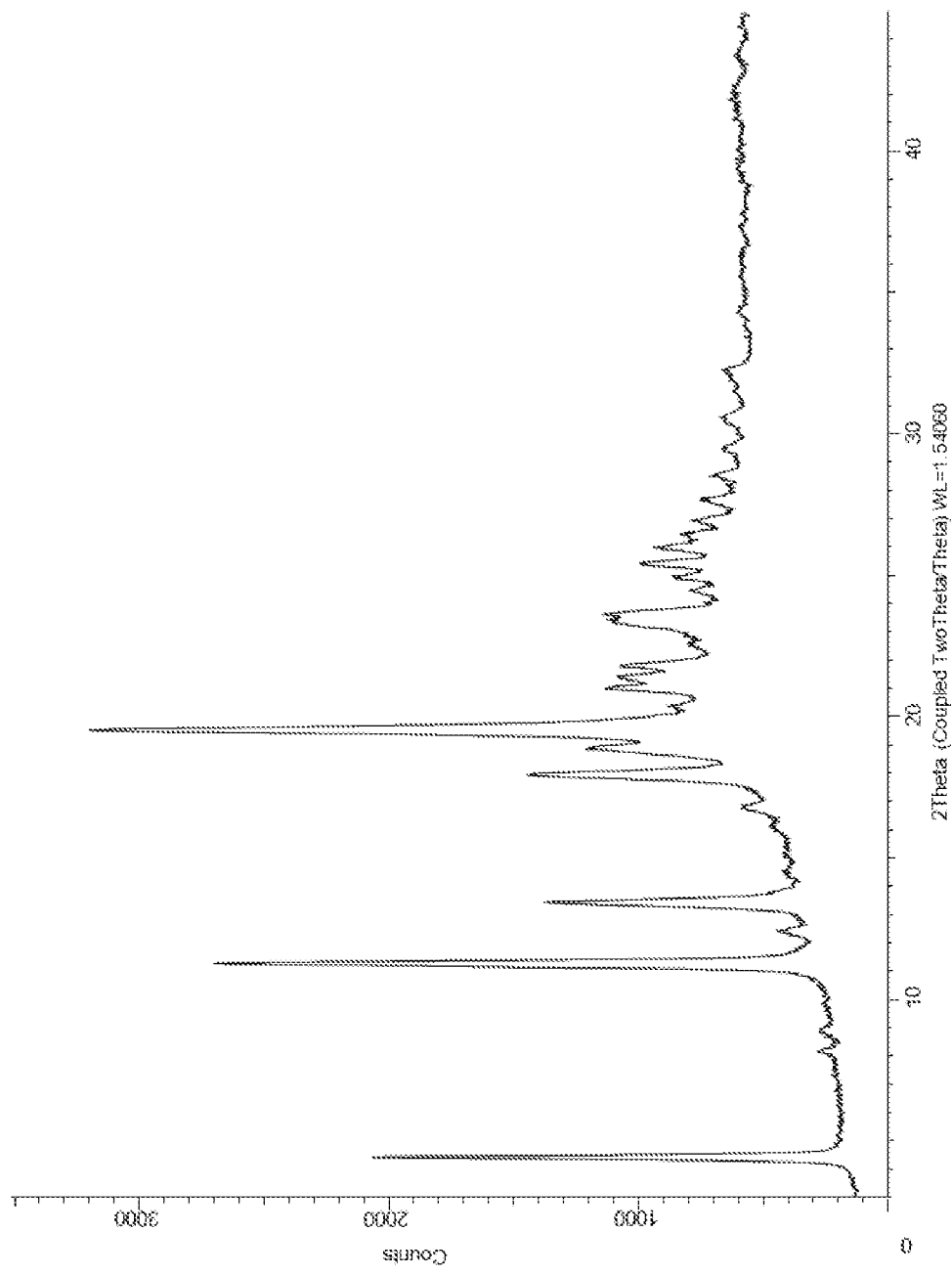
Figure 3. X-ray powder diffraction spectrum of crystalline Form B

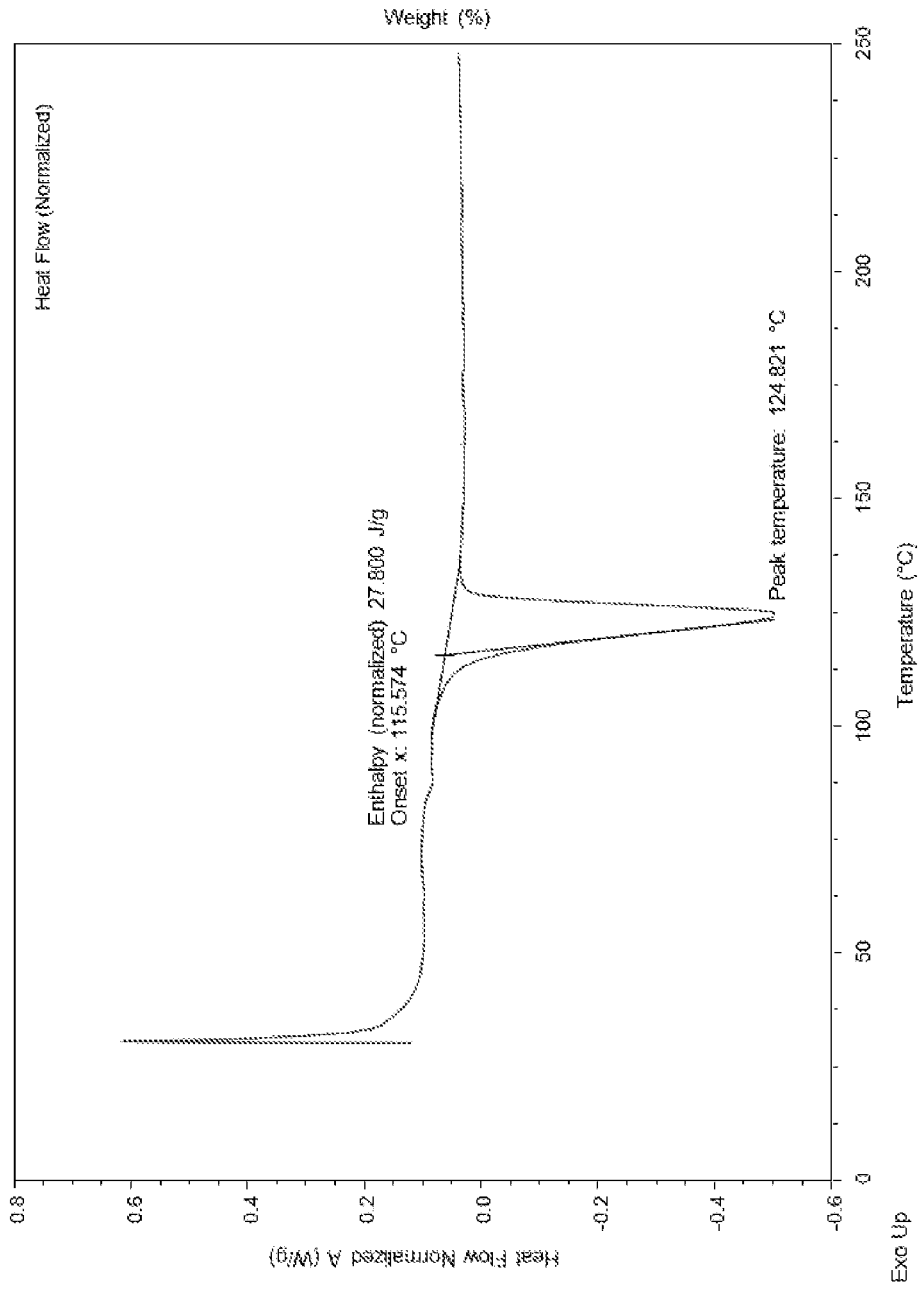
Figure 4. DSC thermogram of crystalline Form B

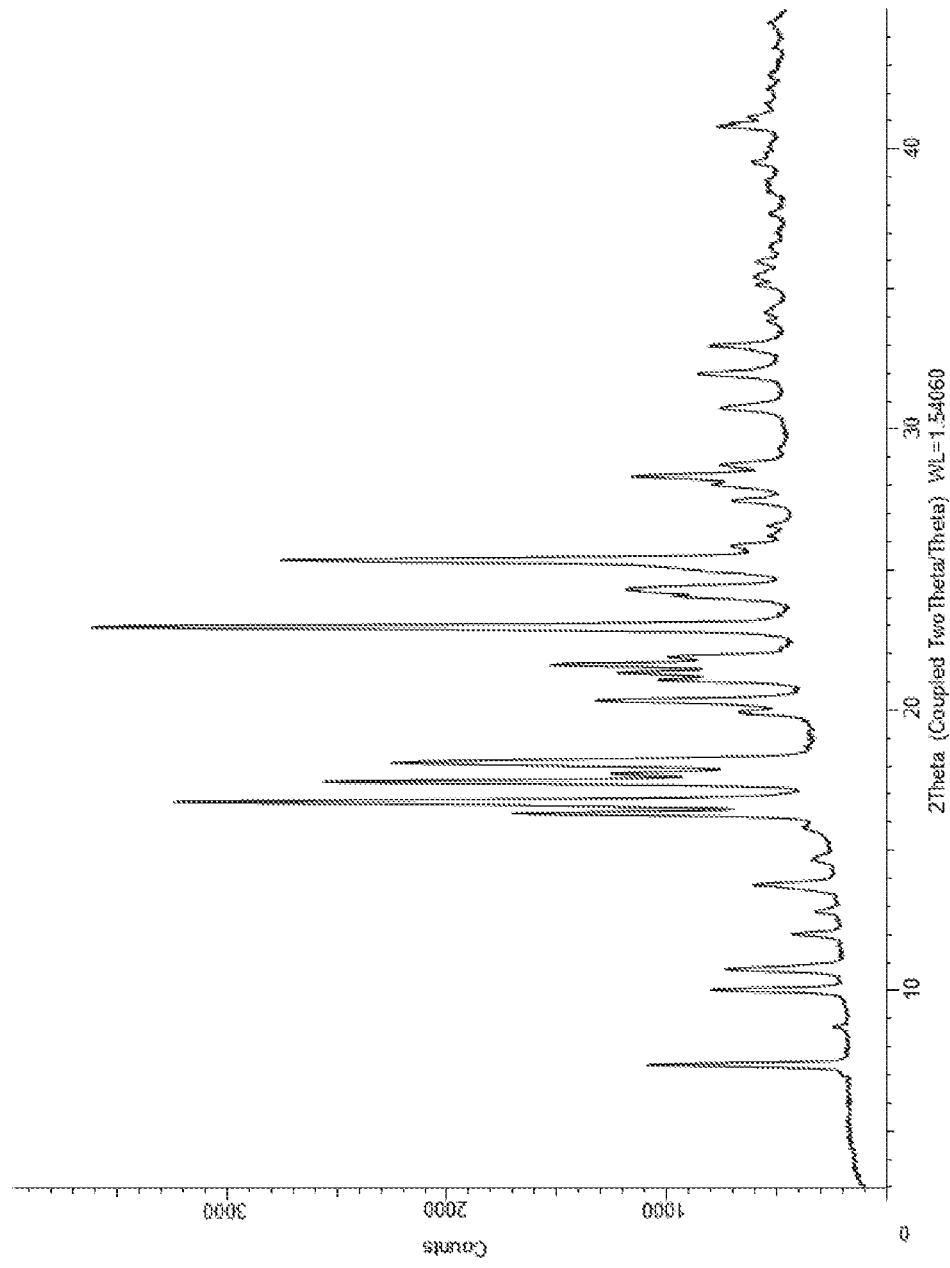
Figure 5. X-ray powder diffraction spectrum of crystalline Monohydrate Form H$_A$

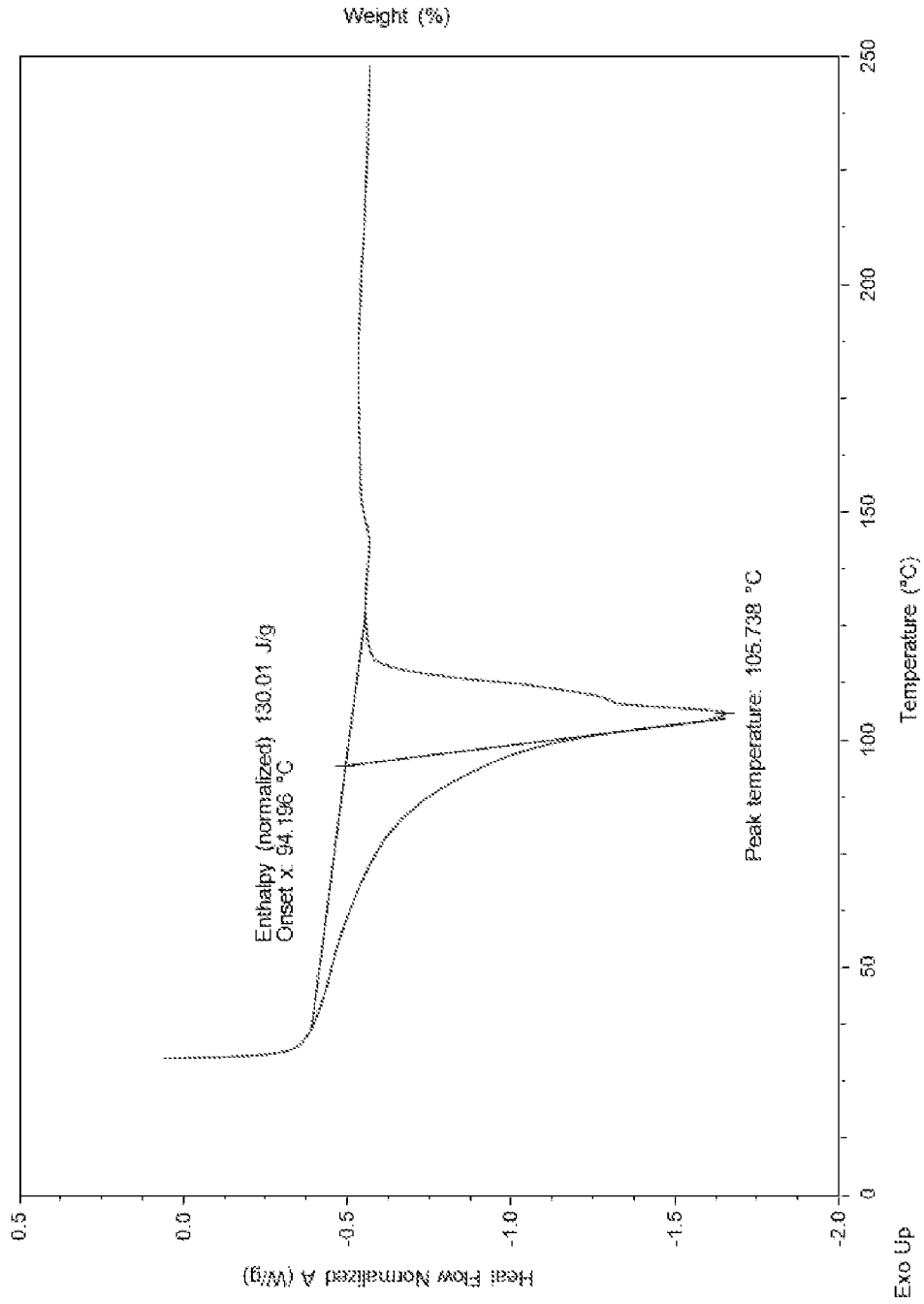
Figure 6. DSC thermogram of crystalline Monohydrate Form H_A

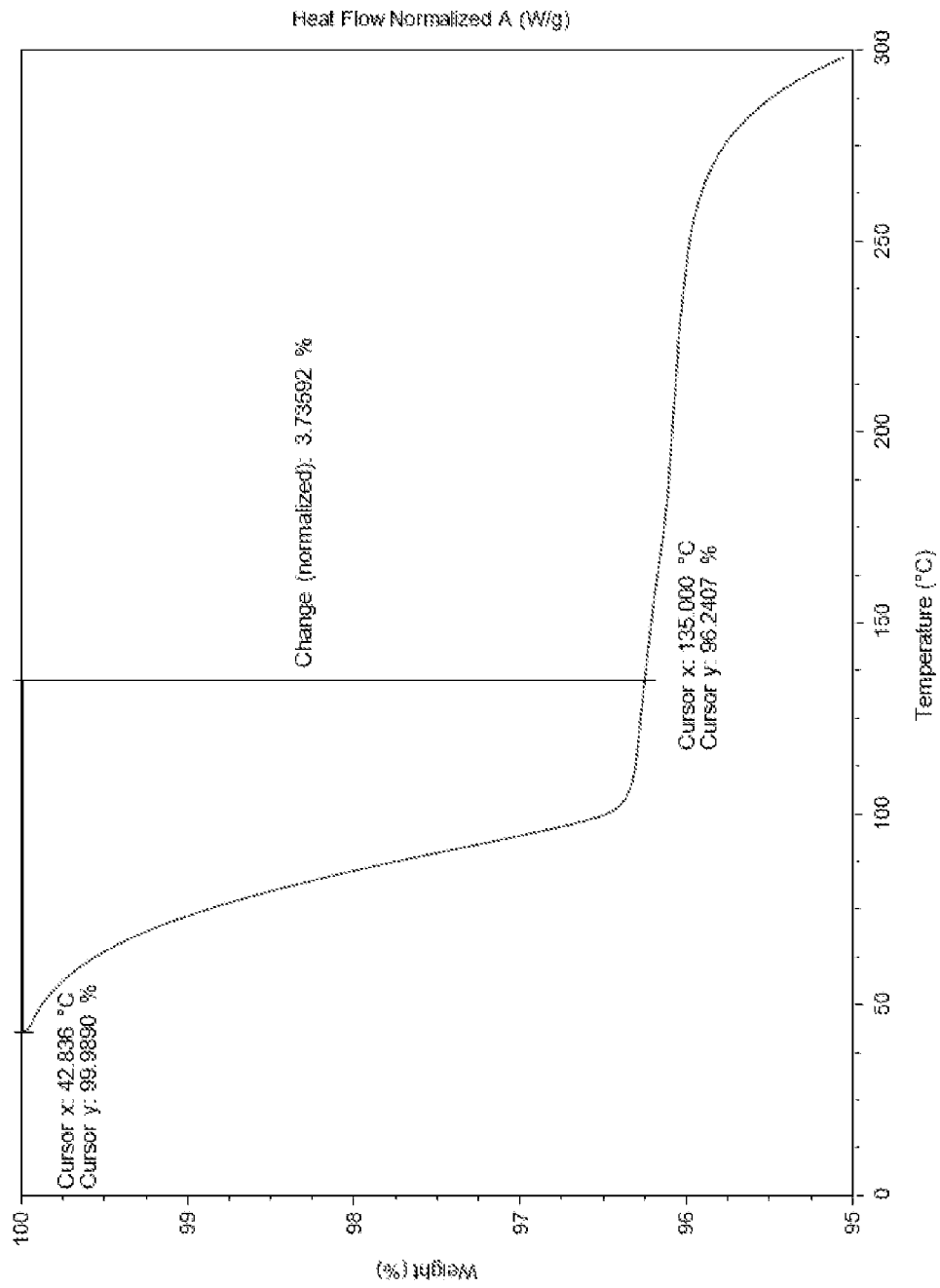

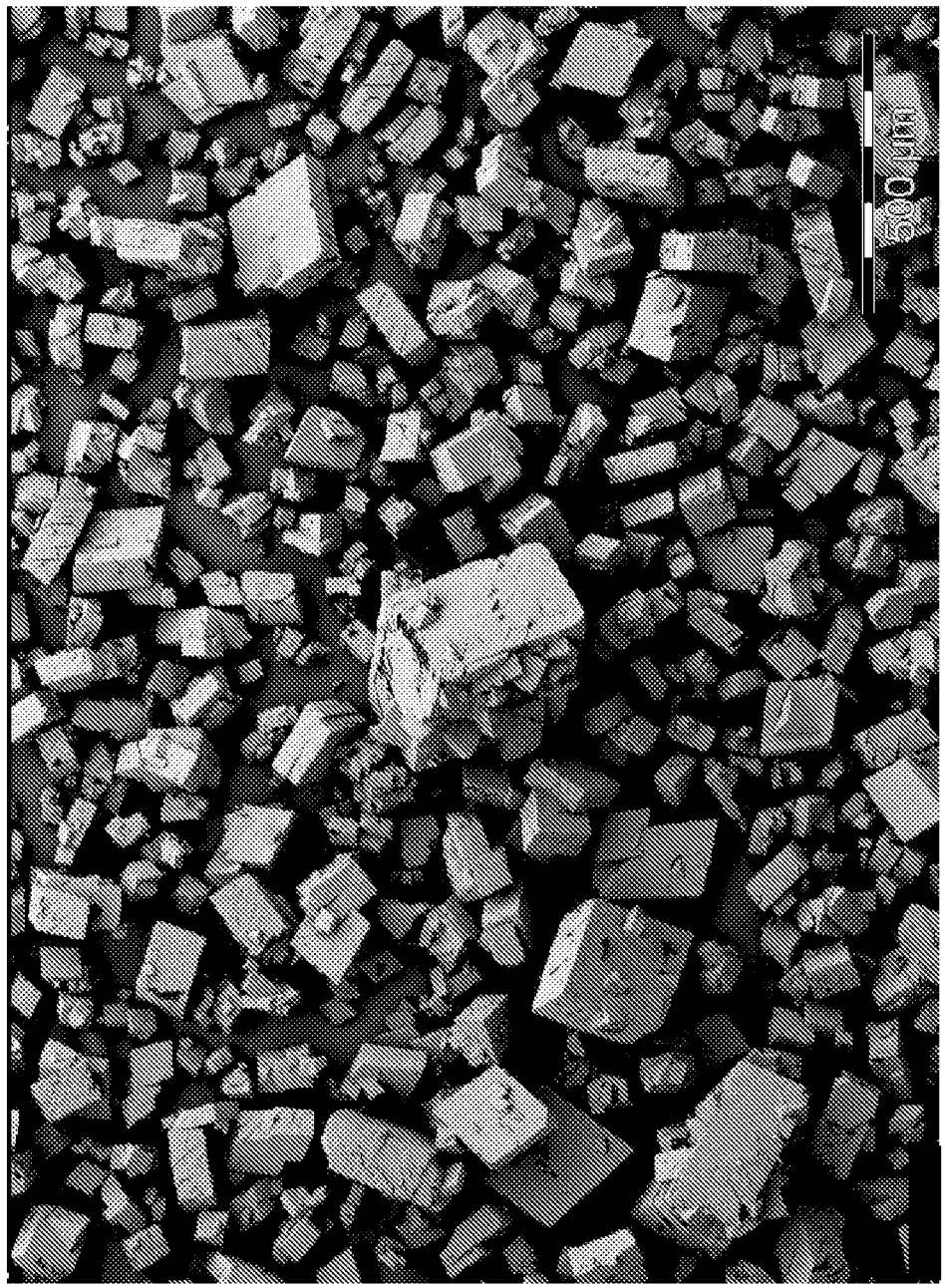
Figure 8. SEM image of crystalline Monohydrate Form $H_A$

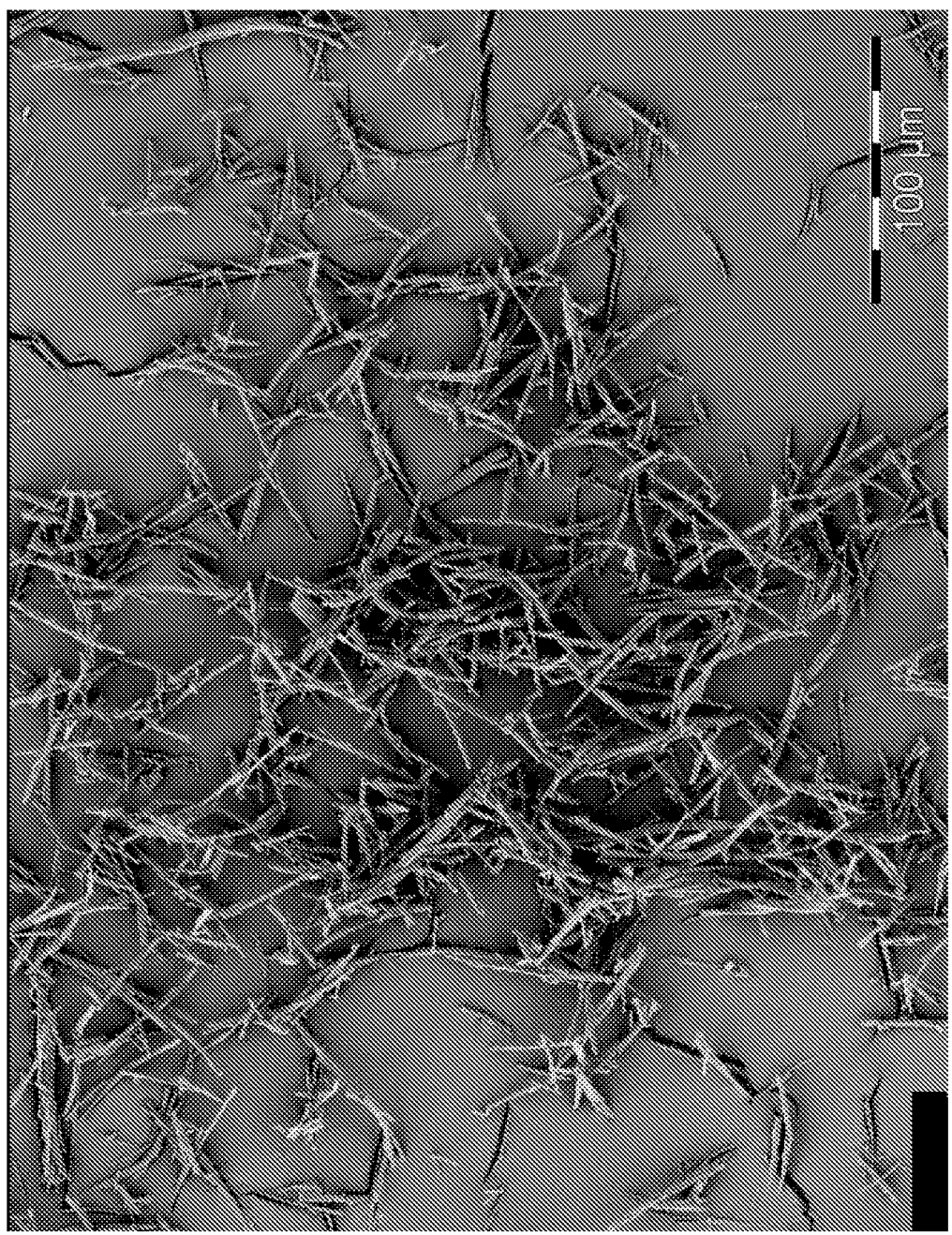
Figure 9. SEM image of crystalline Form A

CRYSTALLINE FORMS OF N-(3-(2-(2-HYDROXYETHOXY)-6-MORPHOLINOPYRIDIN-4-YL)-4-METHYLPHENYL)-2 (TRIFLUOROMETHYL)ISONICOTINAMIDE AS RAF INHIBITORS FOR THE TREATMENT OF CANCER

RELATED APPLICATIONS

This application is a U.S. National Phase filing of International Application Serial No. PCT/IB2020/054491 filed 12 May 2020, which claims priority to PCT/CN2019/086595 filed 13 May 2019, which is incorporated in its entirety herein.

FIELD OF INVENTION

The present invention relates to crystalline forms of N-(3-(2-(2-hydroxyethoxy)-6-morpholinopyridin-4-yl)-4-methylphenyl)-2-(trifluoromethyl)isonicotinamide. The present invention also relates to a pharmaceutical composition comprising the crystalline forms, as well of methods of making and methods of using the crystalline forms in the treatment of a proliferative disease, particularly a cancer.

BACKGROUND

N-(3-(2-(2-hydroxyethoxy)-6-morpholinopyridin-4-yl)-4-methylphenyl)-2-(trifluoromethyl)isonicotinamide was originally described in WO 2014/151616 as the compound of Example 1156. It is a Raf inhibitor, particularly a CRAF- and BRAF-inhibitor, having the structure of Formula (I):

Formula (I)

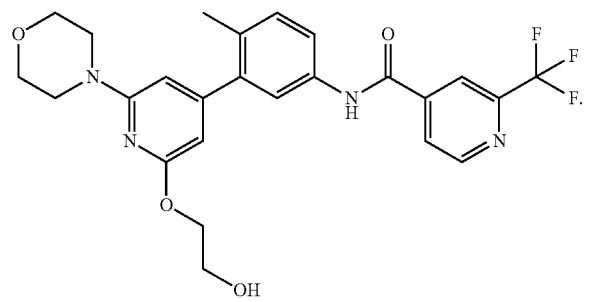

The compound of Formula (I) is thus useful in the treatment of various cancers, in particular in the treatment of cancers harboring MAPK pathway alterations.

The RAS/RAF/MEK/ERK or MAPK pathway is a key signaling cascade that drives cell proliferation, differentiation, and survival. Dysregulation of this pathway underlies many instances of tumorigenesis. Aberrant signaling or inappropriate activation of the MAPK pathway has been shown in multiple tumor types, including melanoma, lung and pancreatic cancer, and can occur through several distinct mechanisms, including activating mutations in RAS and BRAF. RAS is a superfamily of GTPases, and includes KRAS (v-Ki-ras2 Kirsten rat sarcoma viral oncogene homolog), which is a regulated signaling protein that can be turned on (activated) by various single-point mutations, which are known as gain of function mutations. The MAPK pathway is frequently mutated in human cancer with KRAS and BRAF mutations being among the most frequent (approximately 30%).

The compound of Formula (I) may therefore be useful in the treatment of cancers such as KRAS-mutant NSCLC (non-small cell lung cancer), KRAS-mutant pancreatic cancer (e.g. KRAS-mutant pancreatic ductal adenocarcinoma (PDAC)), KRAS-mutant CRC (colorectal cancer), and NRAS-mutant melanoma.

It is not yet possible to predict whether a particular compound or salt of a compound will form polymorphs in the first place or whether any such polymorphs will be suitable for commercial use in a pharmaceutical composition which is suitable for administering to patients in need thereof, or which polymorphs will display desirable properties.

This is because different solid state forms of a particular compound often possess different properties. Solid state forms of an active pharmaceutical ingredient (API) thus play an important role in determining the ease of preparation, hygroscopicity, stability, solubility, storage stability, ease of formulation, rate of dissolution in gastrointestinal fluids and in vivo bioavailability of the therapeutic drug.

Processing or handling of the active pharmaceutical ingredient during the manufacture and/or during the formulation process may also be improved when a particular solid form of the API is used. Desirable processing properties mean that certain solid forms can be easier to handle, better suited for storage, and/or allow for better purification, compared to previously known solid forms or mixtures of solid forms of the API provided in the prior art.

There is thus a need for solid forms of the compound of Formula (I) with properties, which will render them suitable for use in drug substance and drug product development. In accordance with the present invention, there are provided solid forms of the compound of Formula (I) that provide handling properties suitable for manufacture on industrial scale, along with methods of producing these polymorphs. Provided herein are solid forms with well-defined morphologies, and good powder properties like high bulk density, good flowability and/or good compactibility etc. In particular, it has been found that the Monohydrate Form $H_A$ allows improved handling and processing of the crystals during manufacturing.

SUMMARY

The present invention provides crystalline forms of N-(3-(2-(2-hydroxyethoxy)-6-morpholinopyridin-4-yl)-4-methylphenyl)-2-(trifluoromethyl)isonicotinamide in free form.

Thus, in a first aspect provided herein is a crystalline form of N-(3-(2-(2-hydroxyethoxy)-6-morpholinopyridin-4-yl)-4-methylphenyl)-2-(trifluoromethyl)isonicotinamide in monohydrate Form $H_A$.

In a second aspect, provided herein is a process for the preparation of the polymorph form Monohydrate $H_A$, which Formula (I) comprising the steps:
(i) suspending the Compound of Formula (I) in a water miscible solvent:water mixture;
(ii) heating the mixture up to about 100° C.;
(iii) separating at least a part of the crystals obtained from the mother liquor;
(iv) optionally washing the isolated crystals; and
(v) recovering the Monohydrate Form $H_A$.

In a third aspect provided herein is a crystalline form of N-(3-(2-(2-hydroxyethoxy)-6-morpholinopyridin-4-yl)-4-methylphenyl)-2-(trifluoromethyl)isonicotinamide in Form A.

In a fourth aspect provided herein is a crystalline form of N-(3-(2-(2-hydroxyethoxy)-6-morpholinopyridin-4-yl)-4-methylphenyl)-2-(trifluoromethyl)isonicotinamide in Form B.

In a fifth aspect provided herein is a pharmaceutical composition comprising a crystalline compound of Formula (I) (e.g. Monohydrate Form $H_A$, or the crystalline Form A, or the crystalline Form B) and at least one pharmaceutically acceptable carrier or diluent.

In a sixth aspect, provided herein is the crystalline Monohydrate Form $H_A$, or the crystalline Form A, or the crystalline Form B, for use as a medicament.

In a seventh aspect, provided herein is the crystalline Monohydrate Form $H_A$, or the crystalline Form A, or the crystalline Form B, for use in the treatment of cancer.

In an eight aspect, provided herein is the use of a crystalline compound of formula I (e.g., polymorph Form A or Form B or Monohydrate $H_A$) in the manufacture of a medicament for the treatment of cancer.

In a ninth aspect, provided herein is a method of treatment of cancer, comprising administering to a subject in need thereof a therapeutically effective amount of a crystalline compound of Formula (I) (e.g. polymorph Form A or Form B or Monohydrate $H_A$).

In a tenth aspect, provided herein is an amorphous form of a crystalline compound of Formula (I), preferably in substantially pure form, a pharmaceutical composition comprising this amorphous form, and its use in the treatment of a cancer as described herein.

BRIEF DESCRIPTION OF THE DRAWINGS

FIG. 1 shows the X-ray powder diffraction spectrum of crystalline Form A.

FIG. 2 shows the DSC thermogram of crystalline Form A.

FIG. 3 shows the X-ray powder diffraction spectrum of crystalline Form B.

FIG. 4 shows the DSC thermogram of crystalline Form B.

FIG. 5 shows X-ray powder diffraction spectrum of crystalline Monohydrate Form $H_A$.

FIG. 6 shows the DSC thermogram of crystalline Monohydrate Form $H_A$.

FIG. 7 shows the TGA thermogram of crystalline Monohydrate Form $H_A$.

FIG. 8 shows the SEM image of crystalline Monohydrate Form $H_A$.

FIG. 9 shows the SEM image of crystalline Form A.

DETAILED DESCRIPTION OF THE INVENTION

The present invention provides crystalline forms of N-(3-(2-(2-hydroxyethoxy)-6-morpholinopyridin-4-yl)-4-methylphenyl)-2-(trifluoromethyl)isonicotinamide in free form (the compound of formula I), which are described and characterised herein.

The compound N-(3-(2-(2-hydroxyethoxy)-6-morpholinopyridin-4-yl)-4-methylphenyl)-2-(trifluoromethyl) isonicotinamide can be represented by the following chemical structure according to Formula (I)

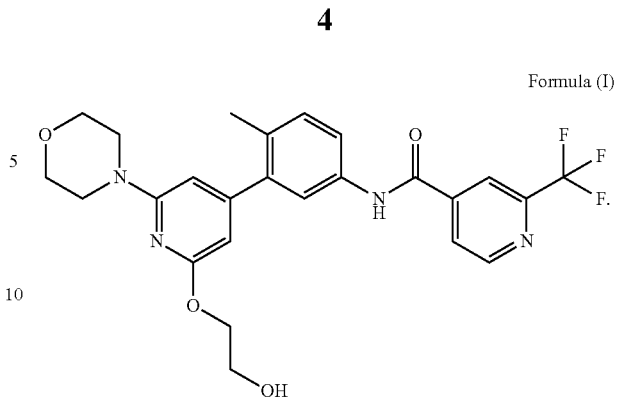

Formula (I)

For manufacturing pharmaceutical compounds and their formulations, it is important that the active compound is in a form that can be conveniently handled and processed in order to obtain a commercially viable, reliable, and reproducible manufacturing process. The compound of formula (I) and can be produced in various solid forms, depending on the conditions used to produce, purify or crystallize the material.

Crystalline Forms A, B and Monohydrate $H_A$ of N-(3-(2-(2-hydroxyethoxy)-6-morpholinopyridin-4-yl)-4-methylphenyl)-2-(trifluoromethyl)isonicotinamide of the present invention possess favorable physicochemical properties for a drug substance intended for use in an oral solid dosage form. In particular, Monohydrate $H_A$ surprisingly provides improved handling and processing properties in comparison to Form A or Form B, which in turn enables an improved manufacturing process.

It has now been found that surprisingly the process developed enables the manufacture of solid Form Monohydrate $H_A$ in cube-like shaped crystals (sometimes aggregated crystals) with very favourable and advantageous processing properties, as described herein. In terms of improved powder handling properties, coarser and cube-like shaped crystals of Modification $H_A$ are advantageous.

Further, as described herein, fine-tuning of powder properties like bulk density, crystal size and shape of Monohydrate $H_A$ is possible by controlling key process parameters, e.g. choice of organic solvent and water, addition temperature.

Crystalline Forms A, B and Monohydrate $H_A$ of N-(3-(2-(2-hydroxyethoxy)-6-morpholinopyridin-4-yl)-4-methylphenyl)-2-(trifluoromethyl)isonicotinamide of the present invention may be characterized by analytical methods well known in the field of the pharmaceutical industry for characterizing solids. Such methods comprise but are not limited to PXRD, DSC and TGA. It may be characterized by one of the aforementioned analytical methods or by combining two or more of them. In particular, Forms A, B and Monohydrate $H_A$ of the compound of Formula (I) of the present invention may be characterized by any one of the following embodiments or by combining two or more of the following embodiments.

The present invention provides a monohydrate of N-(3-(2-(2-hydroxyethoxy)-6-morpholinopyridin-4-yl)-4-methylphenyl)-2-(trifluoromethyl)isonicotinamide in free form, which is described and characterised herein. Monohydrate Form $H_A$ can be defined by reference to one or more characteristic signals that result from analytical measurements including, but not necessarily limited to: the X-ray powder diffraction pattern of FIG. 5, or the differential scanning calorimetry of FIG. 6. Monohydrate Form $H_A$ can also be defined by reference to one or more of the following characteristic signals:

In one embodiment, the Monohydrate Form $H_A$ exhibits an X-ray powder diffraction pattern having at least one, two or three characteristic peaks expressed in degrees 2-Theta (° 2θ) at angles of 7.3°+/−0.2°, 10.7°+/−0.2° and 23.0°+/−0.2° when measured using CuKα radiation. In another embodiment, the Monohydrate Form $H_A$ exhibits at least one, two or three characteristic peaks at angles of 7.3°+/−0.2°, 10.7°+/−0.2°, 16.3°+/−0.2°, 16.7°+/−0.2° and 23.0°+/−0.2° when measured using CuKα radiation. In another embodiment, the Monohydrate Form $H_A$ exhibits at least one, two, three, four or five characteristic peaks at angles of 7.3°+/−0.2°, 10.7°+/−0.2°, 16.3°+/−0.2°, 16.7°+/−0.2°, 17.4°+/−0.2°, 23.0°+/−0.2°, 24.3°+/−0.2°, 25.3°+/−0.2°, 28.3°+/−0.2° and 32.0°+/−0.2° when measured using CuKα radiation. In yet a further embodiment, the Monohydrate Form $H_A$ exhibits an X-ray powder diffraction pattern substantially in accordance with FIG. 5 and Table 5 when measured using CuKα radiation.

In one embodiment, the Monohydrate Form $H_A$ is present in substantially pure form.

In one embodiment, the Monohydrate Form $H_A$ exhibits a differential scanning calorimetry thermogram having a characteristic (endothermic) peak expressed in units of ° C. with an onset temperature of about 94° C. In another embodiment, the Monohydrate Form $H_A$ exhibits a differential scanning calorimetry thermogram substantially in accordance with FIG. 6.

In one embodiment, the Monohydrate Form $H_A$ is characterized by TGA having a curve which shows a mass loss of about 3.7%, based on the weight of the crystalline form, when heated from about 43 to 135° C. at a rate of 10 K/min, in accordance with FIG. 7. In another embodiment, the Monohydrate Form $H_A$ exhibits a TGA thermogram substantially in accordance with FIG. 7.

Preferably, the invention relates to a crystalline form of N-(3-(2-(2-hydroxyethoxy)-6-morpholinopyridin-4-yl)-4-methylphenyl)-2-(trifluoromethyl)isonicotinamide in Monohydrate Form $H_A$ characterized by exhibiting cube-like shaped crystals.

In a further embodiment, the Monohydrate Form $H_A$ has a cubic crystal shape, e.g., as determined by scanning electron microscopy.

In another embodiment, the present invention provides a crystalline form of N-(3-(2-(2-hydroxyethoxy)-6-morpholinopyridin-4-yl)-4-methylphenyl)-2-(trifluoromethyl)isonicotinamide in Form A. Polymorph Form A can be defined by reference to one or more characteristic signals that result from analytical measurements including, but not necessarily limited to: the X-ray powder diffraction pattern of FIG. 1, or the differential scanning calorimetry of FIG. 2. Polymorph form A can also be defined by reference to one or more of the following characteristic signals:

In one embodiment, the polymorph Form A exhibits an X-ray powder diffraction pattern having at least one, two or three characteristic peaks expressed in degrees 2-Theta (° 2θ) at angles of 5.8°+/−0.2°, 11.7°+/−0.2° and 14.8°+/−0.2° when measured using CuKα radiation. In another embodiment, the polymorph Form A exhibits at least one, two or three characteristic peaks at angles of 5.8°+/−0.2°, 11.7°+/−0.2°, 14.8°+/−0.2°, 15.2°+/−0.2° and 18.7°+/−0.2° when measured using CuKα radiation. In another embodiment, the polymorph Form A exhibits at least one, two, three, four or five characteristic peaks at angles of 5.8°+/−0.2°, 10.0°+/−0.2°, 11.7°+/−0.2°, 12.6°+/−0.2°, 13.1°+/−0.2°, 14.8°+/−0.2°, 15.2°+/−0.2°, 18.7°+/−0.2°, 20.2°+/−0.2° and 25.1°+/−0.2° when measured using CuKα radiation. In yet a further embodiment, the polymorph Form A exhibits an X-ray powder diffraction pattern substantially in accordance with FIG. 1 and Table 3 when measured using CuKα radiation.

In one embodiment, the polymorph Form A is present in substantially pure form.

In one embodiment, the polymorph Form A exhibits a differential scanning calorimetry thermogram having a characteristic (endothermic) peak expressed in units of ° C. with an onset temperature of about 142° C. In another embodiment, the polymorph Form A exhibits a differential scanning calorimetry thermogram substantially in accordance with FIG. 2.

In another embodiment, the present invention provides a crystalline form of N-(3-(2-(2-hydroxyethoxy)-6-morpholinopyridin-4-yl)-4-methylphenyl)-2-(trifluoromethyl)isonicotinamide in Form B. Polymorph Form B can be defined by reference to one or more characteristic signals that result from analytical measurements including, but not necessarily limited to: the X-ray powder diffraction pattern of FIG. 3, or the differential scanning calorimetry of FIG. 4. Polymorph form B can also be defined by reference to one or more of the following characteristic signals:

In one embodiment, the polymorph Form B exhibits an X-ray powder diffraction pattern having at least one, two or three characteristic peaks expressed in degrees 2-Theta (° 2θ) at angles of 5.8°+/−0.2°, 11.7°+/−0.2° and 14.8°+/−0.2° when measured using CuKα radiation. In another embodiment, the polymorph Form B exhibits at least one, two or three characteristic peaks at angles of 5.8°+/−0.2°, 11.7°+/−0.2°, 14.8°+/−0.2°, 15.2°+/−0.2° and 18.7°+/−0.2° when measured using CuKα radiation. In another embodiment, the polymorph Form B exhibits at least one, two, three, four or five characteristic peaks at angles of 5.8°+/−0.2°, 10.0°+/−0.2°, 11.7°+/−0.2°, 12.6°+/−0.2°, 13.1°+/−0.2°, 14.8°+/−0.2°, 15.2°+/−0.2°, 18.7°+/−0.2°, 20.2°+/−0.2° and 25.1°+/−0.2° when measured using CuKα radiation. In yet a further embodiment, the polymorph Form B exhibits an X-ray powder diffraction pattern substantially in accordance with FIG. 3 and Table 4 when measured using CuKα radiation.

In one embodiment, the polymorph Form B is present in substantially pure form.

In one embodiment, the polymorph Form B exhibits a differential scanning calorimetry thermogram having a characteristic (endothermic) peak expressed in units of ° C. with an onset temperature of about 116° C. In another embodiment, the polymorph Form B exhibits a differential scanning calorimetry thermogram substantially in accordance with FIG. 4.

Definitions

In the context of the present invention the following definitions have the indicated meaning, unless explicitly stated otherwise:

The term "free form" refers to the compound N-(3-(2-(2-hydroxyethoxy)-6-morpholinopyridin-4-yl)-4-methylphenyl)-2-(trifluoromethyl)isonicotinamide as the free base.

As used herein the term "room temperature" refers to a temperature in the range of from 20 to 30° C.

Measurements are taken under standard conditions common in the art, unless specified otherwise.

As used herein, the term "measured at a temperature in the range of from 20 to 30° C." refers to a measurement under standard conditions. Typically, standard conditions mean a temperature in the range of from 20 to 30° C., i.e. at room temperature. Standard conditions can mean a temperature of about 22° C.

The term "substantially the same" with reference to X-ray diffraction peak positions means that typical peak position and intensity variability are taken into account. For example, one skilled in the art will appreciate that the peak positions (2θ) will show some inter-apparatus variability, typically as much as 0.2°. Further, one skilled in the art will appreciate that relative peak intensities will show inter-apparatus variability as well as variability due to degree of crystallinity, preferred orientation, prepared sample surface, and other factors known to those skilled in the art, and should be taken as qualitative measures only. An expression referring to a crystalline Form A having "an X-ray powder diffraction pattern substantially the same as the X-ray powder diffraction pattern shown in Figure X" may be interchanged with an expression referring to a crystalline Form A having "an X-ray powder diffraction pattern characterised by the representative X-ray powder diffraction pattern shown in Figure X".

One of ordinary skill in the art will also appreciate that an X-ray diffraction pattern may be obtained with a measurement error that is dependent upon the measurement conditions employed. In particular, it is generally known that intensities in an X-ray diffraction pattern may fluctuate depending upon measurement conditions employed. It should be further understood that relative intensities may also vary depending upon experimental conditions and, accordingly, the exact order of intensity should not be taken into account. Additionally, a measurement error of diffraction angle for a conventional X-ray diffraction pattern is typically about 5% or less, and such degree of measurement error should be taken into account as pertaining to the aforementioned diffraction angles. Consequently, it is to be understood that the crystal form of the instant invention is not limited to the crystal form that provides an X-ray diffraction pattern completely identical to the X-ray diffraction pattern depicted in the accompanying FIG. 1 disclosed herein. Any crystal forms that provide X-ray diffraction patterns substantially identical to that disclosed in the accompanying FIG. 1 fall within the scope of the present invention. The ability to ascertain substantial identities of X-ray diffraction patterns is within the purview of one of ordinary skill in the art. Crystalline Monohydrate Form $H_A$ or Form A or Form B of N-(3-(2-(2-hydroxyethoxy)-6-morpholinopyridin-4-yl)-4-methylphenyl)-2-(trifluoromethyl)isonicotinamide of the present invention may be referred to herein as being characterized by graphical data "as shown in" a figure. Such data include, for example, powder X-ray diffraction, DSC and TGA analysis. The person skilled in the art understands that factors such as variations in instrument type, response and variations in sample directionality, sample concentration and sample purity may lead to small variations for such data when presented in graphical form, for example variations relating to the exact peak positions and intensities. However, a comparison of the graphical data in the figures herein with the graphical data generated for another or an unknown solid form and the confirmation that two sets of graphical data relate to the same crystal form is well within the knowledge of a person skilled in the art.

As used herein the term "polymorph" refers to crystalline forms having the same chemical composition but different spatial arrangements of the molecules, atoms, and/or ions forming the crystal.

The terms "dehydrating" or "dehydration" as used herein, describe the at least partial removal of water from the crystal structure of the host molecule.

The terms "anhydrous form" or "anhydrate" as used herein refer to a crystalline solid were no water is cooperated in or accommodated by the crystal structure. Anhydrous forms may still contain residual water, which is not part of the crystal structure but may be adsorbed on the surface or absorbed in disordered regions of the crystal. Typically, an anhydrous form does not contain more than 2.0 w-%, preferably not more than 1.0 w-% of water, based on the weight of the crystalline form.

The term "hydrate" as used herein, refers to a crystalline solid where either water is cooperated in or accommodated by the crystal structure e.g. is part of the crystal structure or entrapped into the crystal (water inclusions). Thereby, water can be present in a stoichiometric or non-stoichiometric amount. For example, a hydrate may be referred to as a hemihydrate or as a monohydrate depending on the water/compound stoichiometry. The water content can be measured, for example, by Karl-Fischer-Coulometry.

As used herein, the term "amorphous" refers to a solid form of a compound that is not crystalline. An amorphous compound possesses no long-range order and does not display a definitive X-ray diffraction pattern with reflections.

As used herein, the term "mother liquor" refers to the solution remaining after crystallization of a solid from said solution.

The term "antisolvent" as used herein refers to liquids which reduce the solubility of N-(3-(2-(2-hydroxyethoxy)-6-morpholinopyridin-4-yl)-4-methylphenyl)-2-(trifluoromethyl)isonicotinamide in a solvent.

As used herein, "substantially pure" or "essentially pure form" when used in reference to a form, e.g. amorphous form, Form A, Form B or Monohydrate $H_A$, means the compound having a purity greater than 90 w-%, including greater than 90, 91, 92, 93, 94, 95, 96, 97, 98, and 99 w-%, and also including equal to about 100 w-% of N-(3-(2-(2-hydroxyethoxy)-6-morpholinopyridin-4-yl)-4-methylphenyl)-2-(trifluoromethyl)isonicotinamide, based on the weight of the compound. The remaining material comprises other form(s) of the compound, and/or reaction impurities and/or processing impurities arising from its preparation. For example, a crystalline form of N-(3-(2-(2-hydroxyethoxy)-6-morpholinopyridin-4-yl)-4-methylphenyl)-2-(trifluoromethyl)isonicotinamide may be deemed substantially pure in that it has a purity greater than 90 w-%, as measured by means that are at this time known and generally accepted in the art, where the remaining less than 10 w-% of material comprises other form(s) of N-(3-(2-(2-hydroxyethoxy)-6-morpholinopyridin-4-yl)-4-methylphenyl)-2-(trifluoromethyl)isonicotinamide and/or reaction impurities and/or processing impurities. Thus in an embodiment, provided is an amorphous form of the compound of formula (I) Form A, Form B or Monohydrate $H_A$, having a purity greater than 90 w-%, including greater than 90, 91, 92, 93, 94, 95, 96, 97, 98, and 99 w-%.

The term "pharmaceutically acceptable excipient" as used herein refers to substances, which do not show a significant pharmacological activity at the given dose and that are added to a pharmaceutical composition in addition to the active pharmaceutical ingredient. Excipients may take the function of vehicle, diluent, release agent, disintegrating agent, dissolution modifying agent, absorption enhancer, stabilizer or a manufacturing aid among others. Excipients may include fillers (diluents), binders, disintegrants, lubricants and glidants.

The terms "filler" or "diluent" as used herein refer to substances that are used to dilute the active pharmaceutical ingredient prior to delivery. Diluents and fillers can also serve as stabilizers.

As used herein the term "binder" refers to substances, which bind the active pharmaceutical ingredient and pharmaceutically acceptable excipient together to maintain cohesive and discrete portions.

The terms "disintegrant" or "disintegrating agent" as used herein refers to substances, which, upon addition to a solid pharmaceutical composition, facilitate its break-up or disintegration after administration and permits the release of the active pharmaceutical ingredient as efficiently as possible to allow for its rapid dissolution.

The term "lubricant" as used herein refers to substances, which are added to a powder blend to prevent the compacted powder mass from sticking to the equipment during tableting or encapsulation process. They aid the ejection of the tablet from the dies and can improve powder flow.

The term "glidant" as used herein refers to substances, which are used for tablet and capsule formulations in order to improve flow properties during tablet compression and to produce an anti-caking effect.

The term "effective amount" or "therapeutically effective amount" as used herein with regard to N-(3-(2-(2-hydroxyethoxy)-6-morpholinopyridin-4-yl)-4-methylphenyl)-2-(trifluoromethyl)isonicotinamide encompasses an amount of N-(3-(2-(2-hydroxyethoxy)-6-morpholinopyridin-4-yl)-4-methylphenyl)-2-(trifluoromethyl)isonicotinamide, which causes the desired therapeutic and/or prophylactic effect.

The term "non-hygroscopic" as used herein refers to a compound showing a water uptake of at most 2 w-% in the sorption cycle when measured with GMS (or DVS) at a relative humidity in the range of from 0 to 95% RH and a temperature of $(25.0\pm0.1)$ °C., based on the weight of the compound. Non-hygroscopic is preferably up to 0.2%.

The terms "solid form" or "solid state form" as used herein interchangeably refer to any crystalline and/or amorphous phase of a compound.

Processes

In another aspect, the present invention relates to a process for the preparation of crystalline form Monohydrate $H_A$ of the Compound of Formula (I) of the present invention as defined in any one of the aspects and their corresponding embodiments described above comprising:
(i) suspending the Compound of Formula (I) in a water miscible solvent:water mixture;
(ii) heating the mixture up to about 100° C.;
(iii) separating at least a part of the crystals obtained from the mother liquor;
(iv) optionally washing the isolated crystals; and
(v) recovering the Monohydrate Form $H_A$.

In an embodiment, the process for the preparation of crystalline form Monohydrate $H_A$ of the Compound of Formula (I) of the present invention comprises the steps:
(i) suspending the Compound of Formula (I) in a water miscible solvent:water mixture;
(ii) heating the mixture up to about 100° C.;
(iii) cooling the mixture to room temperature, optionally followed by addition of more water;
(iv) separating at least a part of the crystals obtained from the mother liquor;
(v) optionally washing the isolated crystals; and
(vi) recovering the Monohydrate Form $H_A$ crystals.

Preferably, the mixture of step (ii) is heated to about 40-70° C.

The Compound of Formula (I) starting material can be prepared according to the procedure disclosed in Example 1156 of WO 2014/151616 A1.

The solid starting material provided in step (i) is dissolved in a water miscible solvent:water mixture, for example, the water miscible solvent is acetone, ethanol, methanol, propanol, butanol, isopropyl alcohol, tetrahydrofuran (THF), acetonitrile and the like. Preferably, the water miscible solvent is acetonitrile, acetone, methanol, ethanol, propanol or isopropyl alcohol. Most preferably, the water miscible solvent is acetonitrile, acetone or ethanol. The ratio of solvent:water is preferably 1:2 based on the weight of the solvent:water.

The reaction mixture may be heated to a temperature of about 100° C. and cooled down to about −20° C. Preferably, the mixture of step is heated to about 40-70° C. More preferably, the mixture is heated to 50° C.

Optionally, to the solution or suspension, water can be added to reduce the solubility of the Compound of Formula (I) in the solvent-water mixture.

Heating the mixture in step (ii) can be conducted over a period of about 4 hours. Preferably, the mixture is heated for a period of 2 hours. Preferably, the mixture is heated to 50° C. over a period of 4 hours, preferably over a period of 2 hours.

The cooling step can be performed over a period of at least 4 hours, e.g. at least 6 hours, e.g. 4-24 hours. Preferably, the cooling step is performed over a period of about 4 hours.

Once Monohydrate Form $H_A$ is obtained in essentially pure form (e.g. in essentially pure form, this can be determined as described below, by withdrawing samples from the mixture and analyzing the sample by powder X-ray diffraction), at least a part of the crystals are separated from the mother liquor. Preferably, the crystals are separated from their mother liquor by any conventional method such as filtration, centrifugation, solvent evaporation or decantation, more preferably by filtration or centrifugation and most preferably by filtration.

Optionally, in a further step the isolated crystals are washed with a suitable solvent, for example an organic solvent and/or water or a mixture thereof. Suitable organic solvents include, but are not limited to water, acetone, acetonitrile, methanol, ethanol, propanol, butanol, isopropyl alcohol, tetrahydrofuran and the like.

The obtained crystals are then dried. Drying may be performed at a temperature of about 20-80° C., preferably, about 30 to 70° C. Typically, drying can performed at about room temperature. Depending on the temperature employed, drying may be performed for a period in the range of from about 2 to 72 hours.

Preferably, drying is performed at a temperature of about 40° C. from about 4 to 24 hours, preferably about 7 to 15 hours, more preferably about 8 hours at 40° C. Drying may be performed at ambient pressure and/or under reduced pressure. Preferably, drying is performed under reduced pressure, for example 0-100 mbar. More preferably, drying is performed under reduced pressure, at a temperature of about 40° C. for about 8 hours.

In another aspect, the present invention relates to a process for the preparation of crystalline Form A of the Compound of Formula (I) of the present invention as defined in any one of the aspects and their corresponding embodiments described above comprising:
(i) suspending the Compound of Formula (I) in an organic solvent;
(ii) addition of an antisolvent;

(iii) isolating the crystals obtained;
(iv) optionally washing the isolated crystals; and
(v) recovering the Form A crystals.

In one embodiment, the process for the preparation of crystalline Form A of the Compound of Formula (I) of the present invention comprises the steps of:
(i) suspending the Compound of Formula (I) in an organic solvent;
(ii) filtering the mixture by hot filtration;
(iii) addition of an antisolvent;
(iv) slurrying at a temperature range of from 10° C.-80° C.;
(v) isolating the crystals obtained;
(vi) optionally washing the isolated crystals; and
(vii) recovering the Form A crystals.

The solid starting material provided in step (i) is dissolved in an organic solvent, for example, ethyl acetate, isopropyl acetate, THF, isopropyl alcohol. However, most preferably ethyl acetate is used.

Addition of an antisolvent is preferably a hydrocarbon solvent. For example, the hydrocarbon solvent can be n-hexane, n-heptane, cycloalkane, e.g. cyclohexane. Preferably, the antisolvent is n-heptane.

Once, Form A is obtained (e.g. in essentially pure form—this can be determined as described below, e.g., by withdrawing samples from the slurry and analyzing the sample by powder X-ray diffraction), at least a part of the crystals is separated from the mother liquor. Preferably, the crystals are separated from their mother liquor by any conventional method such as filtration, centrifugation, solvent evaporation or decantation, more preferably by filtration or centrifugation and most preferably by filtration.

Optionally, in a further step the isolated crystals are washed with a suitable solvent, for example an organic solvent. Suitable organic solvents comprise but are not limited to acetone, acetonitrile, methanol, ethanol, isopropyl alcohol, acetonitrile, n-heptane, ethyl acetate or mixtures thereof. Preferably, the crystals are washed with a mixture of n-heptane and ethyl acetate. The fraction of n-heptane may be from 90 to 50 percent by weight, preferably from 80 to 60 percent by weight.

Drying may be performed at a temperature of about 20 to 100° C., preferably 40 to 80° C., more preferably at about 60° C. Typically, drying is performed at about room temperature. Most preferably, drying is performed at 60° C. Depending on the temperature employed, drying may be performed for a period in the range of from about 6 to 72 hours, preferably from about 12 to 20 hours, more preferably for about 15 hours. Drying may be performed at ambient pressure or under reduced pressure. Preferably, drying is performed under reduced pressure, e.g. 0-100 mbar.

In another aspect, the present invention relates to a process for the preparation of crystalline Form B of the Compound of Formula (I) of the present invention as defined in any one of the aspects and their corresponding embodiments described above comprising:
(i) suspending the Compound of Formula (I) in a suitable solvent;
(ii) acidifying the resultant mixture;
(iii) slurrying the mixture;
(iv) neutralising the mixture using a suitable base;
(v) optionally washing the mixture obtained in step (iv); and
(vi) recovering the Form B.

The solid starting material provided in step (i) is slurried in a solvent, for example, acetonitrile. Most preferably acetonitrile is the only solvent present in the slurry.

Acidification is performed at 5 to 10° C. using a suitable acid, such as, for example, HCl. Slurrying is conducted for at least 5 hours, such as 5 hours, 7 hours, 10 hours at a temperature of 30 to 15° C. Preferably, slurrying is conducted over a period of 5-10 hours. Neutralisation is achieved using a suitable base, such as, for example, sodium bicarbonate. Once Form B is obtained (e.g. in essentially pure form; this can be done as described below, e.g., by withdrawing from the slurry and analyzing the sample by powder X-ray diffraction). the crystals can be recovered. Preferably, the crystals are separated from their mother liquor by any conventional method such as filtration, centrifugation, solvent evaporation or decantation, more preferably by filtration or centrifugation and most preferably by filtration.

Optionally, in a further step the isolated crystals are washed with a suitable solvent, for example an organic solvent. Suitable organic solvents comprise but are not limited to acetonitrile, n-heptane, ethyl acetate.

Slurrying encompasses any kind of movement of the solid material suspended in the solvent caused by, but not limited to e.g. agitation, stirring, mixing, shaking, vibration, sonication, wet milling and the like. Slurrying is conducted in total for about 1 day, or longer. The skilled person may monitor the conversion of the applied solid form of N-{3-[2-(Hydroxyethoxy)-6-(morpholin-4-yl)pyridin-4-yl]-4-methylphenyl}-2-(trifluoromethyl)pyridine-4-carboxamide to the required polymorphic form, e.g. Form B, by withdrawing samples from the slurry and analyzing the sample by powder X-ray diffraction.

Drying may be performed at a temperature of about 20 to 100° C., preferably 40 to 80° C., more preferably at about 60° C. Typically, drying is performed at about room temperature. Most preferably, drying is performed at 60° C. Depending on the temperature employed, drying may be performed for a period in the range of from about 6 to 72 hours, preferably from about 12 to 20 hours, more preferably for about 15 hours. Drying may be performed at ambient pressure or under reduced pressure. Preferably, drying is performed under reduced pressure, e.g. 0-100 mbar.

Alternatively, Form A may be provided and suspended in dichloromethane for 1 to 5 days at a temperature of 40 to 60° C., to produce Form B.

Pharmaceutical Compositions and Use

In a further aspect the present invention relates to the use of the crystalline Form A, or Form B or Monohydrate $H_A$ of N-(3-(2-(2-hydroxyethoxy)-6-morpholinopyridin-4-yl)-4-methylphenyl)-2-(trifluoromethyl)isonicotinamide of the present invention as defined in any one of the aspects and their corresponding embodiments described above for the preparation of a pharmaceutical composition.

In yet another aspect, the present invention relates to a pharmaceutical composition comprising the crystalline Form A, or Form B or Monohydrate $H_A$ of N-(3-(2-(2-hydroxyethoxy)-6-morpholinopyridin-4-yl)-4-methylphenyl)-2-(trifluoromethyl)isonicotinamide as defined in any one of the aspects and their corresponding embodiments described above, preferably in a predetermined and/or effective amount, and at least one pharmaceutically acceptable excipient.

Preferably, the predetermined and/or effective amount of the crystalline Form A, or Form B or Monohydrate $H_A$ of N-(3-(2-(2-hydroxyethoxy)-6-morpholinopyridin-4-yl)-4-methylphenyl)-2-(trifluoromethyl)isonicotinamide as defined in any one of the aspects and their corresponding embodiments described above can be in unit dosage of about 50-1200 mg (e.g., per day). Hence, crystalline Form A, or Form B or Monohydrate $H_A$ of N-(3-(2-(2-hydroxyethoxy)-6-morpholinopyridin-4-yl)-4-methylphenyl)-2-(trifluoromethyl)isonicotinamide as defined in any one of the aspects and their corresponding embodiments described above can be administered at a unit dosage of about 50 mg, about 100 mg, about 150 mg, about 200 mg, about 250 mg, about 300 mg, about 350 mg, about 400 mg, about 450 mg, about 500 mg about 550 mg, about 600 mg, about 650 mg, about 700 mg, about 750 mg, about 800 mg, about 850 mg, about 900 mg, about 950 mg, about 1000 mg, about 1050 mg, about 1100 mg, about 1150 mg or about 1200 mg. The unit dosage may be administered once daily, or twice daily, or three times daily, or four times daily, with the actual dosage and timing of administration determined by criteria such as the patient's age, weight, and gender; the extent and severity of the cancer to be treated; and the judgment of a treating physician. Preferably, the unit dosage of crystalline Form A, or Form B or Monohydrate $H_A$ of N-(3-(2-(2-hydroxyethoxy)-6-morpholinopyridin-4-yl)-4-methylphenyl)-2-(trifluoromethyl)isonicotinamide is administered once daily. In another preferred embodiment, the unit dosage of crystalline Form A, or Form B or Monohydrate $H_A$ of N-(3-(2-(2-hydroxyethoxy)-6-morpholinopyridin-4-yl)-4-methylphenyl)-2-(trifluoromethyl)isonicotinamide is administered twice daily.

Crystalline Form A, or Form B or Monohydrate $H_A$ of N-(3-(2-(2-hydroxyethoxy)-6-morpholinopyridin-4-yl)-4-methylphenyl)-2-(trifluoromethyl)isonicotinamide may in particular be administered at a dose of 100 mg once daily (QD), 200 mg once daily, 300 mg once daily, 400 mg once daily, 800 mg once daily or 1200 mg once daily (QD). Crystalline Form A, or Form B or Monohydrate $H_A$ of N-(3-(2-(2-hydroxyethoxy)-6-morpholinopyridin-4-yl)-4-methylphenyl)-2-(trifluoromethyl)isonicotinamide may also be administered at a dose of 100 mg, 200 mg twice daily, 400 mg twice daily or 600 mg twice daily (BD). The dosages quoted herein may apply to the administration of crystalline Form A, or Form B or Monohydrate $H_A$ of N-(3-(2-(2-hydroxyethoxy)-6-morpholinopyridin-4-yl)-4-methylphenyl)-2-(trifluoromethyl)isonicotinamide as monotherapy (single agent) or as part of a combination therapy.

When describing a dosage herein as 'about' a specified amount, the actual dosage can vary by up to 5-7% from the stated amount: this usage of 'about' recognizes that the precise amount in a given dosage form may differ slightly from an intended amount for various reasons without materially affecting the in vivo effect of the administered compound. The unit dosage of the c-Raf inhibitor may be administered once daily, or twice daily, or three times daily, or four times daily, with the actual dosage and timing of administration determined by criteria such as the patient's age, weight, and gender; the extent and severity of the cancer to be treated; and the judgment of a treating physician.

The at least one pharmaceutically acceptable excipient, which is comprised in the pharmaceutical composition of the present invention, is preferably selected from the group consisting of fillers, diluents, binders, disintegrants, lubricants, glidants and combinations thereof.

In a preferred embodiment, the pharmaceutical composition comprising the crystalline Form A, or Form B or Monohydrate $H_A$ of N-(3-(2-(2-hydroxyethoxy)-6-morpholinopyridin-4-yl)-4-methylphenyl)-2-(trifluoromethyl)isonicotinamide as defined in any one of the aspects and their corresponding embodiments described above is an oral solid dosage form. Preferably, the oral solid dosage form is selected from the group consisting of tablets, capsules, etc.

In a particular preferred embodiment, the oral dosage form is a tablet or a capsule, most preferably a tablet.

In a further aspect, the present invention relates to the crystalline Form A, or Form B or Monohydrate $H_A$ of N-(3-(2-(2-hydroxyethoxy)-6-morpholinopyridin-4-yl)-4-methylphenyl)-2-(trifluoromethyl)isonicotinamide or the pharmaceutical composition comprising the same as defined in any one of the above described aspects and their corresponding embodiments for use as a medicament.

In yet another aspect, the present invention relates to the crystalline Form A, or Form B or Monohydrate $H_A$ of N-(3-(2-(2-hydroxyethoxy)-6-morpholinopyridin-4-yl)-4-methylphenyl)-2-(trifluoromethyl)isonicotinamide or the pharmaceutical composition comprising the same as defined in any one of the above described aspects and their corresponding embodiments for use in the treatment of a proliferative disease, particularly a cancer.

In one embodiment, the cancer is non-small cell lung cancer (NSCLC), melanoma, pancreatic ductal adenocarcinoma (PDAC), cervical cancer, ovarian cancer or colorectal cancer (CRC). In one embodiment, proliferative disease is selected from a solid tumor that harbors one or more Mitogen-activated protein kinase (MAPK) alteration(s), KRAS-mutant NSCLC (non-small cell lung cancer), NRAS-mutant melanoma, KRAS- and/or BRAF-mutant NSCLC, KRAS- and/or BRAF-mutant ovarian cancer, KRAS-mutant pancreatic cancer (e.g. KRAS-mutant pancreatic ductal adenocarcinoma (PDAC)).

In another aspect, the invention concerns a method of treating and/or preventing a proliferative disease, particularly a cancer, said method comprising administering an effective amount of the Form A, or Form B, or the Monohydrate $H_A$ of N-(3-(2-(2-hydroxyethoxy)-6-morpholinopyridin-4-yl)-4-methylphenyl)-2-(trifluoromethyl)isonicotinamide as defined in the above described aspects and their corresponding embodiments to a patient in need of such a treatment. In one embodiment, the cancer is non-small cell lung cancer (NSCLC), melanoma, pancreatic ductal adenocarcinoma (PDAC), cervical cancer, ovarian cancer or colorectal cancer (CRC). In one embodiment, proliferative disease is selected from a solid tumor that harbors one or more Mitogen-activated protein kinase (MAPK) alteration(s), KRAS-mutant NSCLC (non-small cell lung cancer), NRAS-mutant melanoma, KRAS- and/or BRAF-mutant NSCLC, KRAS- and/or BRAF-mutant ovarian cancer, KRAS-mutant pancreatic cancer (e.g. KRAS-mutant pancreatic ductal adenocarcinoma (PDAC)).

In another preferred aspect, provided herein is a method for the treatment of disorders mediated by Raf, in particular B-Raf or C-Raf, and/or MAPK pathway alterations, comprising administering to a patient in need of such treatment an effective amount of a crystalline compound of Formula (I) (e.g. polymorph Form A or Form B or Monohydrate $H_A$).

In a further aspect, the invention relates to the use of a crystalline compound of formula I (e.g., polymorph Form A or Form B or Monohydrate $H_A$) for the preparation of a medicament for the treatment of disorders mediated by Raf, in particular B-Raf or C-Raf, and/or MAPK pathway alterations.

EXAMPLES

The following Examples illustrate various aspects of the invention. Example 1 outlines how Compound 1 may be prepared. Example 2 shows how it may be crystallised to produce Form A. Examples 3 and 4 describe the XRPD and DSC analysis of Form A. Example 5 describes the process of preparation of Form B and the corresponding XRPD data are shown in Example 6. Example 7 shows the DSC data of Form B. Examples 8, 9, 10 and 11 describe the process of making Monohydrate Form $H_A$, and the XRPD, DSC and TGA analysis of Monohydrate Form $H_A$. Examples 12 and 13 describe the stability testing of Monohydrate $H_A$ and Form B. Examples 14 and 15 show the water activity experiments of Monohydrate Form $H_A$ and Form A. Example 16 shows the solubility data of Monohydrate $H_A$, Form A and Form B. The release data of Monohydrate $H_A$ and Form A are shown in Example 17. Example 18 shows competitive slurry experiments of Form A and Form B. Example 19 describes the behaviour of Form A and B under compression.

Abbreviations

API active pharmaceutical ingredient
d day(s)
DCM dichloromethane
DMSO dimethylsulfoxide
dp dimensions and particle size
DMF N,N-dimethylformamide
DSC differential scanning calorimetry
DVS dynamic vapor sorption
Equiv equivalent
GMS gravimetric moisture sorption
h hour
HPLC high performance liquid chromatography
IPA isopropyl alcohol
KF Karl-Fischer
LOQ limit of quantitation
min. or min minute
MC methylcellulose
MS mass spectrometry
NMR nuclear magnetic resonance
PSD particle size dimension
RH or rh relative humidity
Rt retention time (min)
RT room temperature
THF tetrahydrofuran
TFA trifluoroacetic acid
TGA thermogravimetric analysis
UPLC ultra performance liquid chromatography
v/v by volume
vol-% volume percent
w/w by weight
w-% weight percent
WL copper Kα radiation wavelength (λCu=1.5406 Å)
XRPD powder X-ray diffraction

| UPLC Method | |
| --- | --- |
| Instrument | Water Acquity UPLC |
| Column Chemistry | ACQUITY UPLC BEH C18 |
| Column Manufacture | Waters |
| Particle Size (um) | 1.7 |
| Dimensions (mm) | 2.1 × 100 |
| Column Temperature (° C.) | 30 |
| Flow Rate (mL/minute) | 0.50 |
| Injection Volume (uL) | 1 |
| Sample Solvent | Acetonitrile/Water (75:25) |
| Sample Concentration (ug/mL) | 500 |
| Wavelength (nm) | 250 |
| Mobile Phase A | 0.05% TFA in 95% Water/5% Acetonitrile |
| Mobile Phase B | 0.05% TFA in 95% Acetonitrile/5% Water |
| Run Time (minutes) | 12.5 |
| Gradient | |
| Minutes | % B |
| Initial | 0 |
| 9.02 | 100 |
| 9.80 | 100 |
| 10.13 | 0 |
| 12.41 | 0 |

XRPD Method:

X-ray powder diffraction (XRPD) analysis of all polymorph forms was performed using a Bruker D8 Discover x-ray diffractometer with XYZ stage. Measurements were taken at about 40 kV and 1 mA under the following conditions:

TABLE 1

| XRPD | |
| --- | --- |
| Detector | VANTEC-500 including controller 19" |
| Step size, resolution | 0.02 degrees |
| Measuring slice | 0.3 mm and 0.2 mm |
| Scan time | 2 min |
| X-ray optics | Iµs MONTEL optic for Cu |
| Source slit | Fixed, 1 mm |
| Detector distance | ~30 cm |

The X-ray diffraction pattern was recorded at room temperature between 2° and 45° (2-theta) with CuK$_α$ radiation for identification of the whole pattern.

DSC Method:

Differential scanning calorimetry (DSC) analysis of all polymorph forms was performed using a Discovery Differential Scanning Calorimeter from TA instruments under the following conditions:

TABLE 2

| DSC | |
| --- | --- |
| Instrument | TA Discovery DSC |
| Temperature range | 30° C.-250° C. |
| Scan rate | 10 K/min |
| Nitrogen flow | 20 mL/min |

Example 1: Synthesis of Compound of Formula (I)

The preparation of Compound 1 is described in WO 2014/151616 A1 (Example 1156).

Example 2: Process of Preparation of Form A

To a reactor was charged crude N-(3-(2-(2-hydroxyethoxy)-6-morpholinopyridin-4-yl)-4-methylphenyl)-2-(trifluoromethyl)isonicotinamide (4.62 kg), ethyl acetate (16.5 kg). The reaction mixture was stirred for about 15 min. until a clear solution was obtained, then the solution was filtered and transferred to another reactor. To the mixture was charged n-heptane (37.2 kg) with internal temperature maintained 63±3° C., over at least 2 h. The mixture was then cooled to 27±3° C., over at least 5 h. The mixture was aged for no less than 6 h with internal temperature maintained at 27±3° C. The mixture was filtered and washed with n-heptane/ethyl acetate (7.8 kg/2.6 kg). The wet cake was dried under vacuum setting (1-109 mbar) at 60° C. for 15 h to afford crystals of Form A.

Example 3: XRPD Analysis of Form A

Crystalline Form A was analysed by XRPD and the ten most characteristic peaks are shown in Table 3 (see also FIG. 1).

TABLE 3

| 2-theta in degrees | relative intensity in % |
|---|---|
| 5.8 | 25.8 |
| 10.0 | 46.9 |
| 11.7 | 19.0 |
| 12.6 | 12.4 |
| 13.1 | 12.3 |
| 14.8 | 100.0 |
| 15.2 | 43.2 |
| 18.7 | 37.2 |
| 20.2 | 40.1 |
| 25.1 | 14.7 |

Example 4: DSC Analysis of Form A

Crystalline Form A was found to have an onset of melting at about 142° C. (see FIG. 2) according to the DSC method outlined above and Table 2.

Form A is thermodynamically more stable and has a higher melting point and melting enthalpy than Form B.

Example 5: Process of Preparation of Form B

To an ice cooled (5 to 10° C.) solution of N-(4-methyl-3-(2-morpholino-6-(2-((tetrahydro-2H-pyran-2-yl)oxy)ethoxy)pyridin-4-yl)phenyl)-2-(trifluoromethyl)isonicotinamide (prepared according to WO 2014/151616 A1 (Example 1156)) (3.65 kg, 6.22 mol) in acetonitrile (18.25 L) was added 2M HCl (18.25 L, 5 vol) drop wise between 5 to 10° C. After complete addition the reaction mixture was slowly allowed to warm to 25 to 30° C. and stirred for 6 h. The progress of the reaction was monitored by HPLC. The reaction mixture was cooled to 15 to 20° C. and basified to pH=7-7.5 using saturated sodium bicarbonate solution between 15 to 20° C. The reaction mixture was stirred for 30 min at 15 to 20° C., diluted with ethyl acetate (36.5 L, 10 vol), stirred for about 5 min and the layers were separated. The aqueous layer was extracted with ethyl acetate (1×5 vol), the combined organic layer was washed with water (1×10 vol), brine (1×10 vol), dried over sodium sulphate, and filtered to give crystals of Form B as the residue.

Example 6: XRPD Analysis of Form B

Crystalline Form B was analysed by XRPD and the ten most characteristic peaks are shown in Table 4 (see also FIG. 3).

TABLE 4

| 2-theta in degrees | relative intensity in % |
|---|---|
| 4.4 | 74.1 |
| 11.3 | 93.8 |
| 13.4 | 39.3 |
| 18.0 | 34.6 |
| 18.9 | 23.1 |

TABLE 4-continued

| 2-theta in degrees | relative intensity in % |
|---|---|
| 19.5 | 100.0 |
| 21.0 | 17.0 |
| 21.8 | 13.7 |
| 23.6 | 16.8 |
| 25.4 | 11.5 |

Example 7: DSC Analysis of Form B

Crystalline Form B was found to have an onset of melting at about 116° C. (see FIG. 4) according to the DSC method outlined above and Table 2.

Example 8: Process of Preparation of Monohydrate Form $H_A$

To 3 g of Form A in a 50 mL flask was added 20 mL of acetone:water (1:1 (v/v) mixture). The resulting mixture was heated to 60° C. Stirring was continued at 60° C. for 2 hours (clear solution was observed), and slowly cooled to RT over 4 hours (suspension was observed). The mixture was stirred at RT for a further 16-20 hours. The solid was separated via suction filtration, washed with 5 mL acetone:water (1:1 (v/v) mixture), and the filter cake was dried at 40° C. under vacuum for 8 hours. Crystalline monohydrate form $H_A$ was obtained as an off-white solid.

Scale up: The reactor was charged with 3.6 kg of crude N-(3-(2-(2-hydroxyethoxy)-6-morpholinopyridin-4-yl)-4-methylphenyl)-2-(trifluoromethyl)isonicotinamide and 18 kg of ethanol-water 94:6 (w/w) mixture. The content was stirred and heated to 62° C. until a clear solution was obtained. After cooling to 50° C., 36 kg of water was added over at least 10 hours. After further cooling to 10° C. over at least 7 hours and maintaining for at least 8 hours the solids were filtered off, washed and dried at 30° C. under vacuum for at least 21 hours, to provide crystalline monohydrate form $H_A$ as a free flowing powder.

Example 9: XRPD Analysis of Monohydrate Form $H_A$

Crystalline Monohydrate Form $H_A$ was analysed by XRPD and the ten most characteristic peaks are shown in Table 5 (see also FIG. 5).

TABLE 5

| 2-theta in degrees | relative intensity in % |
|---|---|
| 7.3 | 28.5 |
| 10.7 | 16.6 |
| 16.3 | 43.6 |
| 16.7 | 92.7 |
| 17.4 | 70.5 |
| 23.0 | 100.0 |
| 24.3 | 22.7 |
| 25.3 | 72.6 |
| 28.3 | 21.4 |
| 32.0 | 11.0 |

Example 10: DSC Analysis of Monohydrate Form $H_A$

DSC analysis of Crystalline Monohydrate Form $H_A$ shows an endothermic event from about 35° C. to 135° C. and shows an onset of dehydration at about 94° C. (see FIG. 6) according to the DSC method outlined above and Table 2.

Example 11: TGA Analysis of Monohydrate Form $H_A$

Crystalline Monohydrate Form $H_A$ was analysed by thermogravimetric analysis (TGA) using a Discovery Thermogravimetric Analysis Calorimeter from TA instruments under the following conditions (see Table 6).

TABLE 6

| TGA | |
|---|---|
| Instrument | TA Discovery TGA |
| Temperature range | 42° C.-300° C. |
| Scan rate | 10 K/min |
| Nitrogen flow | 20 mL/min |

The TGA analysis for Crystalline Monohydrate Form $H_A$ shows about 3.7% loss of mass between about 43° C. and 135° C., see FIG. 7. Karl Fischer titration analysis shows a water content of 3.5%, corresponding to one equivalent, thus the monohydrate.

Example 12: Stability Testing of Monoydrate $H_A$

As shown in the Table below, Monohydrate Form $H_A$ is highly stable in bulk, e.g. up to 80° C. over an extended period of time. No notable change in chemical purity, nor change in XRPD, nor change in TGA, was observed. Monohydrate Form $H_A$ is also stable upon light exposure, e.g. 1200 kLuxh for 12 h, and is also stable upon compression, grinding and wet granulation with water.

| | Monohydrate HA | | | |
|---|---|---|---|---|
| Test Conditions | UPLC | | | TGA (%) Weight loss |
| Solid state | | CL | XRPD | at 175° C. |
| Initial Purity (%) | 99.72 | yellow | Highly crystalline | 3.68 |
| 1 week/80° C., glass vials with screw caps DP (%) | | | | |
| Sample 1 | 0.27 | A | No change | 3.60 |
| Sample 2 | 0.27 | A | No change | 3.56 |
| 2 weeks/80° C., glass vials with screw caps | | | | |
| Sample 1 | 0.29 | A | No change | 3.67 |
| Sample 2 | 0.29 | A | No change | 3.76 |
| 2 weeks/50° C., glass vials with screw caps | | | | |
| Sample 1 | 0.29 | A | No change | 3.76 |
| Sample 2 | 0.33 | A | No change | 3.89 |
| 4 weeks/50° C., glass vials with screw caps | | | | |
| Sample 1 | 0.28 | A | No change | 3.75 |
| Sample 2 | 0.27 | A | No change | 3.63 |
| 1 week/80° C./75% RH, open bottles | | | | |
| Sample 1 | 0.30 | A | No change | 3.76 |
| Sample 2 | 0.26 | A | No change | 3.86 |
| 2 weeks/80° C./75% RH, open bottles | | | | |
| Sample 1 | 0.26 | A | No change | 3.60 |
| Sample 2 | 0.28 | A | No change | 3.66 |
| 2 weeks/50° C./75% RH, open bottles | | | | |
| Sample 1 | 0.27 | A | No change | 3.66 |
| Sample 2 | 0.25 | A | No change | 3.65 |
| 4 weeks/50° C./75% RH, open bottles | | | | |
| Sample 1 | 0.30 | A | No change | 3.78 |
| Sample 2 | 0.27 | A | No change | 3.69 |
| 3 months/40° C./75% RH, open bottles | | | | |
| Sample 1 | 0.53 | A | No change | 3.55 |
| Sample 2 | 0.30 | A | No change | 3.60 |
| Xenon light (approx. 1200 kLuxh) | | | | |
| Sample 1 | 0.36 | A | No change | 3.76 |
| Sample 2 | 0.30 | A | No change | 3.90 |

Remarks
Degradation Products (DP) and Color (CL)
A No change of color
DPs are analyzed by UPLC. They are calculated as area-% products.

Monohydrate Form $H_A$ is highly stable, i.e. no significant change in degradation products and no change in physical form, even at high temperature was observed. Therefore, it can be expected to provide suitable storage properties for processing into a pharmaceutical drug product.

Example 13. Stability Testing of Form B

| | Physical Form Free form | |
|---|---|---|
| Test Conditions | | CL |
| Initial purity (%) | 97.74 | off-white powder |
| | DP % | |
| Solid state, 1 week 80° C., closed container | | |
| Bulk (UPLC) | 2.12 | A |
| Bulk (XRPD) | | no change |
| Solid state, 1 week 80° C./75% r.h. | | |
| Bulk (UPLC) | 3.32 | B |
| Bulk (XRPD) | | changed |
| Solid state, 1 week 50° C., closed container | | |
| Bulk (UPLC) | 2.46 | A |
| Bulk (XRPD) | | no change |
| Solid state, 1 week 50° C./75% r.h. | | |
| Bulk (UPLC) | 2.49 | A |
| Bulk (XRPD) | | no change |
| Xenon light (approx. 1200 kLuxh) | | |
| Bulk (HPLC) | 3.66 | B |
| Bulk (XRPD) | | no change |

Remarks
Degradation Products (DP) and Color (CL)
↓ Suspension
\* Clear solution after stress test
— Test not performed
A No change of color
B Slight discoloration
DPs are analyzed by UPLC. They are calculated as area-% products.

Form B is relatively stable, i.e. no major change in degradation products and no change in physical form, upon exposure to elevated temperature or humidity. Therefore, it can be expected to provide suitable storage properties for processing into a pharmaceutical drug product.

Example 14. Water Activity Experiments of Monohydrate $H_A$

About 10 mg of Form A and Monohydrate $H_A$ (1:1 ratio) were weighed into a vial. A saturated solution of Form A in different organic solvents is prepared. Add a different volume of the saturated solutions and water (total volume 0.5 ml) into the vials, respectively. The mixture was stirred at room temperature (RT) or 50° C.

Cross-seeding compatibility experiments or single form equilibration at different water activity and different temperature to see the impact of both water activity and temperature. The water activity (aw) is the partial vapor pressure of water in a substance divided by the standard state partial vapor pressure of water.

At water activity of 0.3 and 0.5 or higher at room temperature and 50° C., Monohydrate $H_A$ is more stable than Form A. In acetonitrile or acetone with water (1:1) the Monohydrate $H_A$ is more stable than Form A. However, in pure water or heptane, due to poor solubility, both crystal forms are still observed after 5 days equilibration, i.e. Form A remains unchanged and Modification $H_A$ remains unchanged.

Thus, Modification $H_A$ shows advantages with respect to solid form stability upon contact with water over a wide range of conditions.

Form A is only obtained and stable at very low water activity, however, it can maintain its crystal form in pure water for a given period of time. This may enable Form A to be formulated as oral solid dosage form by e.g. granulation with water (see Example 15 below).

Example 15. Water Activity Experiments of Form A

About 100 mg of Form A is equilibrated with 0.5 mL solvent by stirring at RT or 50° C. The slurries are filtered. The wet cake is investigated by XRPD.

TABLE 7

Competition slurry equilibration of Form A and Monohydrate $H_A$ in solvents with different water activity at RT.

| Volume fraction water (%) | Volume fraction IPA (%) | Water activity ($a_w$) | Form A (mg) | Monohydrate $H_A$ (mg) | After 1 d equilibration | After 5 d equilibration |
|---|---|---|---|---|---|---|
| 0 | 100 | 0.000 | 10 | 10 | Form A | Form A |
| 1 | 99 | 0.120 | 10 | 10 | Form A | Form A |
| 3.2 | 96.8 | 0.316 | 10 | 10 | $H_A$ | $H_A$ |
| 6 | 94 | 0.496 | 10 | 10 | $H_A$ | $H_A$ |
| 11 | 89 | 0.699 | 10 | 10 | $H_A$ | $H_A$ |
| 22.8 | 77.2 | 0.900 | 10 | 10 | $H_A$ | $H_A$ |
| 34.1 | 65.9 | 0.949 | 10 | 10 | $H_A$ | $H_A$ |
| 100 | 0 | 1.000 | 10 | 10 | Form A + $H_A$ | Form A + $H_A$ |
| Solvents or solvent mixture | | | | | | |
| Acetonitrile:water = 1:1 | | | 10 | 10 | $H_A$ | $H_A$ |
| Acetone:water = 1:1 | | | 10 | 10 | $H_A$ | $H_A$ |
| Heptane | | | 10 | 10 | Form A + $H_A$ | Form A + $H_A$ |

TABLE 8

Competition slurry equilibration of Form A and Monohydrate $H_A$ in solvents with different water activity at 50° C.

| Volume fraction water (%) | Volume fraction IPA (%) | Water activity ($a_w$) | Form A (mg) | Monohydrate $H_A$ | After 1 d equilibration | After 5 d equilibration |
|---|---|---|---|---|---|---|
| 0 | 100 | 0.000 | 10 | 10 | Form A | Form A |
| 1 | 99 | 0.124 | 10 | 10 | Form A | Form A |
| 3.2 | 96.8 | 0.324 | 10 | 10 | Form A | Form A |
| 6 | 94 | 0.503 | 10 | 10 | $H_A$ | $H_A$ |
| 11 | 89 | 0.701 | 10 | 10 | $H_A$ | $H_A$ |
| 22.8 | 77.2 | 0.892 | 10 | 10 | $H_A$ | $H_A$ |
| 34.1 | 65.9 | 0.941 | 10 | 10 | $H_A$ | $H_A$ |
| 100 | 0 | 1.000 | 10 | 10 | Form A + $H_A$ | Form A + $H_A$ |
| Solvents or solvent mixture | | | | | | |
| Acetonitrile:water = 1:1 | | | 10 | 10 | $H_A$ | $H_A$ |
| Acetone:water = 1:1 | | | 10 | 10 | $H_A$ | $H_A$ |
| Heptane | | | 10 | 10 | Form A + $H_A$ | Form A + $H_A$ |

TABLE 9

Water activity experiments of Form A at RT

| Volume fraction water (%) | Volume fraction IPA (%) | Water activity ($a_w$) | Form A (mg) | After 1 d equilibration | After 5 d equilibration |
|---|---|---|---|---|---|
| 0 | 100 | 0.000 | 100 | Form A | Form A |
| 1 | 99 | 0.120 | 100 | Form A | Form A |
| 3.2 | 96.8 | 0.316 | 100 | Form A + $H_A$ | $H_A$ |
| 6 | 94 | 0.496 | 100 | $H_A$ | $H_A$ |
| 11 | 89 | 0.699 | 100 | $H_A$ | $H_A$ |
| 22.8 | 77.2 | 0.900 | 100 | $H_A$ | $H_A$ |
| 34.1 | 65.9 | 0.949 | 100 | $H_A$ | $H_A$ |
| 100 | 0 | 1.000 | 100 | Form A | Form A |

TABLE 10

Water activity experiments of Form A at 50° C.

| Volume fraction water (%) | Volume fraction IPA (%) | Water activity ($a_w$) | Form A (mg) | After 1 d equilibration | After 5 d equilibration |
|---|---|---|---|---|---|
| 0 | 100 | 0.000 | 100 | Form A | Form A |
| 1 | 99 | 0.124 | 100 | Form A | Form A |
| 3.2 | 96.8 | 0.324 | 100 | Form A | Form A |
| 6 | 94 | 0.503 | 100 | $H_A$ | $H_A$ |
| 11 | 89 | 0.701 | 100 | $H_A$ | $H_A$ |
| 22.8 | 77.2 | 0.892 | 100 | $H_A$ | $H_A$ |
| 34.1 | 65.9 | 0.941 | 100 | $H_A$ | $H_A$ |
| 100 | 0 | 1.000 | 100 | Form A | Form A |

At water activity of 0.3 the conversion of Form A to Monohydrate $H_A$ is slow at room temperature and takes 5 days for complete conversion. In the solvent at water activity 0.3 and 0.5 or higher at room temperature and at 50° C. respectively, Form A converts to Monohydrate $H_A$. In pure water, Form A remains unchanged.

Modification $H_A$ is more stable than Modification A in the aqueous-organic solvent system with water activity more than 0.3 and 0.5 at ambient temperature and 50° C., respectively. However, due to the poor solubility in pure water, the conversion of Modification A to $H_A$ takes a longer equilibration time. Thus, as Form A stays unchanged for a sufficiently long period upon contact with water it can be considered suitable for formulation as an oral solid dosage form, e.g. by granulation with water. The amorphous form remains stable and does not convert to $H_A$ either at ambient humidity or at 92% RH.

Example 16: Solubility of Form A, B, Monohydrate $H_A$

A sample was weighed in a glass vial and solvent added to make a slurry followed by stirring or shaking at 25° C. for 24 hours. The amount of sample and solvents depends on the target concentration, e.g. if the target concentration is 10 mg/mL, the weight of the sample should be 10 mg and the amount of solvent volume should be 1 mL. The solid and liquid are separated by centrifugation at 13000 rpm for 2 minutes with 0.2 μm membrane. The filtrate is then used for the solubility test after appropriate dilution. The diluent is from the UPLC method. The solids obtained after equilibration were analyzed by XRPD after being dried at 40° C. under vacuum for 2 hours. DSC/TGA analysis was conducted for selected samples.

The relative solubilities of the monohydrate $H_A$ and Form A and B of N-(4-methyl-3-(2-morpholino-6-(2-(((tetrahydro-2H-pyran-2-yl)oxy)ethoxy)pyridin-4-yl)phenyl)-2-(trifluoromethyl)isonicotinamide were analysed and the results are shown in the tables below.

TABLE 11

Solubility of Monohydrate $H_A$ in aqueous media at 25° C.
Solubility (approx. at 25° C., mg/ml,
target concentration 10 mg/mL, LOQ = 0.002517 mg/mL)

| Parameter | Solubility (Final pH) | XRPD |
|---|---|---|
| pH 1 (0.1N HCl) | <LOQ (1.06) | No change |
| pH 2 (0.01N HCl) | <LOQ (2.12) | No change |
| pH 4.7 acetate buffer | <LOQ (4.73) | No change |
| pH 6.8 phosphate buffer | <LOQ (6.74) | No change |
| pH 9.0 borate buffer | <LOQ (8.88) | No change |
| SGF (pH 2) | 0.0022 (2.07) | No change |
| FeSSIF (pH 5.8) | 0.0032 (5.69) | No change |
| FaSSIF (pH 6.5) | <LOQ (6.44) | No change |
| Methanol | >10 | — |
| Acetonitrile | >10 | — |
| Octanol | >10 | — |
| Ethanol abs. | >10 | — |
| Dichloromethane | >10 | — |
| Ethyl acetate | >10 | — |
| Water | <LOQ (7.22) | No change |

TABLE 12

Solubility of
Form A and Form B in aqueous and organic solvent media at 25° C.
Solubility at 25° C., mg/mL (Final pH)

|  | Form A | Form B |
|---|---|---|
| 0.1N HCl, pH 1.0 | 0.2929 (1.07) | 1.0264 (1.02) |
| 0.01N HCl, pH 2.0 | 0.0014 (2.16) | 0.1412 (2.04) |
| Acetate buffer, pH 4.7 | <0.0003 (4.82) | <0.0002 (4.78) |
| Phosphate buffer, pH 6.8 | <0.0003 (6.74) | <0.0002 (6.75) |
| Borate buffer, pH 9.0 | <0.0003 (9.01) | <0.0002 (8.97) |
| Water | <0.0003 (8.93) | <0.0002 (8.11) |
| SGF, pH 2.0 | 0.0220 (2.05) | 0.0021 (2.02) |
| FaSSIF, pH 6.5 | 0.0008 (6.45) | 0.0014 (6.91) |
| FeSSIF, pH 5.8 | 0.0413 (5.82) | 0.1370 (6.08) |
| Ethanol | >10 | >10 |
| Heptane | — | <0.0002 |
| Dichloromethane | >10 | >10 |
| Acetonitrile | >10 | >10 |
| Ethyl acetate | >10 | >10 |
| N,N-Dimethylformamide | >10 | >10 |

Among the compared anhydrate crystals, the physical Form B provides higher solubility in several aqueous media, particularly at low pH, e.g. pH 1 or 2. Thus, Form B can be expected to behave advantageously in terms of better dissolution properties as oral solid dosage form, e.g. in the stomach. Both anhydrous crystal Forms A and B are more soluble in aqueous media compared to Modification $H_A$, and may thus be advantageous for use as oral solid dosage form medication.

Example 17: Powder Properties of Modification $H_A$ and Form A

Pilot manufacture batches producing Modification $H_A$ and Form A on kilogram scale were compared for their respective bulk powder properties. The particle size distribution (PSD) was determined according to the corresponding method for release. Other measurements were performed using technical methods known in the art or as described herein.

Method to Determine Particle Size

| | |
|---|---|
| Principle | Fraunhofer light diffraction |
| Reagents | |
| Dispersing aid | Tween 20, Fluka No. 93773, approx. 10% in dispersion liquid |
| Dispersion liquid | Deionized water |
| Equipment | |
| Measuring device | Sympatec HELOS, Sympatec GmbH, Germany |
| Dispersion device | Suspension cell, e.g. SUCELL, Sympatec GmbH, Germany |
| Conditions | |
| Measuring device | |
| Focal length | 200 mm (R4) or 500 mm (R5) or 1000 mm (R6) |
| Optical concentration | ≥5% |
| Duration of measurement | 20 s |
| Dispersion device | |
| Stirrer speed | 50-70% |
| Pump speed | 70-90% |
| Ultrasonication time | 0 s, 10 s, 20 s, 30 s . . . etc. until an appropriate deagglomeration is achieved |

Procedure

A few drops of the dispersing aid were added to an appropriate amount of test substance. The mixture was mixed intensively, e.g. on a vortex mixer, in order to wet the substance thoroughly and to form a smooth and homogeneous paste. The resultant paste was diluted with the dispersion liquid to a final volume of 3-6 ml and the dispersion mixed again. The cumulative volume distribution was determined using a laser light diffraction instrument as stated above. The parameters could be adjusted accordingly so that the test dispersion is representative, homogeneous and well dispersed.

Particle sizes were determined at the undersize values of 10%, 50% and 90% (×10, ×50, ×90), and additional values in question, from the cumulative volume distribution.

TABLE 13

| Drug substance form | Modification A | Monohydrate $H_A$ |
|---|---|---|
| XRPD measured during release | Corresponds to Form A | Corresponds to Modification $H_A$ |
| Diameter X of PSD measured during release | X10: 2 μm<br>X50: 8 μm<br>X90: 44 μm | X10: 131 μm<br>X50: 277 μm<br>X90: 414 μm |
| Technical measurement of bulk density with ring shear tester (under no consolidation stress) | 71 kg/m$^3$ | 696 kg/m$^3$ |
| Technical measurement of bulk flowability with ring shear tester (under 1250 Pa normal stress) | 1.45<br>"very cohesive" | 13.7<br>"free flowing" |
| Technical scanning electron micrographs (SEM) images to indicate crystal shape | Needle like (FIG. 9) | Rhombic/cube like (FIG. 8) |

Monohydrate $H_A$ crystals (prepared according to the scale up process of Example 8) are significantly coarser (SEM image in FIG. 8) compared to Modification A crystals (SEM image in FIG. 9), which is quantitatively supported, e.g. by diameter X10: 131 μm vs. 2 μm (>factor 10), obtained through particle size measurement by laser light diffraction.

This leads to significantly larger bulk density of Monohydrate $H_A$ crystals versus Modification A crystals, e.g. 696 kg/m$^3$ versus 71 kg/m$^3$ (approx. factor 10).

This difference in bulk density allows easier powder handling of Monohydrate $H_A$ crystals. This also applies to improved handling of the Monohydrate $H_A$ crystals during manufacturing, i.e. better stirring of the crystal suspension, faster filtration and washing, easier sieving, as well as downstream processing of the Monohydrate $H_A$ crystal powder, i.e. preparation of blend of API with excipients.

The tailoring of powder properties like bulk density, crystal size and shape, etc. of Monohydrate $H_A$ is possible via controlling key process parameters, e.g. choice of organic solvent and water, addition temperature. It is surprising to find that, by careful monitoring of the water addition temperature as described herein, it is also possible to obtain anhydrate Form A (see Table 14). In terms of improved powder handling properties, the coarser cube-like crystals of Modification $H_A$ are advantageous. Hence, Modification $H_A$ shows beneficial properties in that it is possible to tailor the shape of crystals of Modification $H_A$ obtained as described herein.

TABLE 14

| | Dissolve 12 g Compound 1 per 60 g acetone. Add 120 g water over 7 h at 30° C. | Dissolve 12 g Compound 1 per 60 g acetone. Add 120 g water over 7 h at 50° C. | Dissolve 12 g Compound 1 per 60 g isopropyl alcohol. Add 120 g water over 7 h at 30° C. | Dissolve 12 g Compound 1 per 60 g isopropyl alcohol. Add 120 g water over 7 h at 50° C. |
|---|---|---|---|---|
| Process Key Parameters | | | | |
| Drug substance form by XRPD | Corresponds to Form A | Corresponds to Modification $H_A$ | Corresponds to Modification $H_A$ | Corresponds to Modification $H_A$ |
| Diameter X of PSD (method as above) | X10: 1 μm<br>X50: 6 μm<br>X90: 40 μm | X10: 204 μm<br>X50: 469 μm<br>X90: 778 μm | X10: 101 μm<br>X50: 238 μm<br>X90: 390 μm | X10: 156 μm<br>X50: 304 μm<br>X90: 508 μm |
| Typical conditioned bulk density (technical measurement by FT4 Powder Rheometer) | 100 kg/m$^3$ | 650 kg/m$^3$ | 420 kg/m$^3$ | 510 kg/m$^3$ |
| Crystal shape by scanning electron micrographs (SEM) | Needle like | Aggregated cubes | Plate like | Plate like |

27

Example 18. Competitive Slurry Experiments of Form A and Form B

About 50~100 mg of Form A and Form B are weighed by 1:1 ratio into a vial, respectively. Limited solvent is added to the vial to form a suspension. Stirring is maintained at RT for 3 days.

TABLE 15

| Solvents | Form A (mg) | Form B (mg) | XRPD |
| --- | --- | --- | --- |
| Acetone | 100 | 100 | Form A |
| Acetonitrile | 100 | 100 | Solvate |
| Ethyl acetate | 100 | 100 | Form A |
| Ethanol | 50 | 50 | Form A |
| Methanol | 100 | 100 | Form A |
| Heptane | 50 | 50 | Form A + Form B |
| Isopropanol | 50 | 50 | Form A |
| MTBE | 50 | 50 | Form A |
| Toluene | 50 | 50 | Form A |
| Water | 50 | 50 | Form A + $H_A$ |
| Acetone/water 90:10 | 100 | 100 | Mod. $H_A$ |
| Acetone/water 50:50 | 50 | 50 | Mod. $H_A$ |
| ACN/water 90:10 | 100 | 100 | Mod. $H_A$ |
| ACN/water 50:50 | 50 | 50 | Mod. $H_A$ |
| Ethanol/water 90:10 | 100 | 100 | Form A |
| Ethanol/water 50:50 | 50 | 50 | Mod. $H_A$ |

In the competitive slurry experiments of Form A and B, Form A is more stable than Form B in most of the selected organic solvents, i.e. the initial mixtures convert to Form A. Only in acetonitrile a solvate is formed. However, upon equilibration in an aqueous/organic mixture of solvents, Modification $H_A$ was observed and is the most stable form, except in the ethanol/water 90:10 mixture.

Example 19. Behaviour of Form A and Form B Under Compression

The physical form of Form A remains unchanged upon granulation with water or compression. A slight decrease in crystallinity is observed when compressed at pressures of 3 to 6 MPa. Form B did not change XRPD pattern upon grinding, compression and granulation with water.

CONCLUSIONS

Modification $H_A$ exhibits compact particle morphology and high bulk density. In addition, its physical properties, e.g., in terms of shape of crystals obtained can be fine-tuned through crystallization conditions as described herein. Therefore, Modification $H_A$ crystalline form provides several advantages over other forms, such as anhydrous Forms A or B, particularly with respect to challenges encountered during industrial processing, e.g. stirring, separation, drying, powder transportation and mixing of bulk quantities.

Modification $H_A$ may also be beneficial over other solid forms such as anhydrous Form A in other manufacturing processes, e.g, hot melt extrusion conditions. Hence, Modification $H_A$ is specially advantageously suitable for development, especially for drug product manufacturing.

All three forms (A, B and Monohydrate $H_A$) are non-hygroscopic, stable when stored in bulk quantities and are expected to be suitable for long-term storage. All three forms show adequate solubility. Form B is more soluble than Form A which is in turn more soluble than Form $H_A$.

28

The invention claimed is:
1. A crystalline Monohydrate Form $H_A$ of the compound

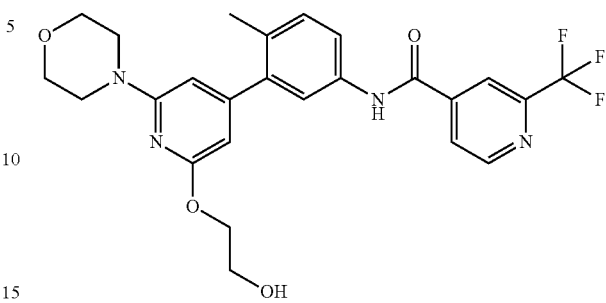

optionally in substantially pure form, wherein the compound has an X-ray powder diffraction pattern with at least four peaks having an angle of refraction 2 theta (θ) values selected from 7.3, 10.7, 16.3, 16.7, and 23.0, wherein the 2 theta (θ) values are measured using CuKα radiation and are plus or minus 0.2° 2θ.

2. The crystalline Monohydrate Form $H_A$ of the compound according to claim 1 which has an X-ray powder diffraction pattern with at least five peaks having an angle of refraction values selected from 7.3, 10.7, 16.3, 16.7, 17.4, 23.0, 24.3, 25.3, 28.3, and 32.0, wherein the 2 theta (θ) values are measured using CuKα radiation and are plus or minus 0.2° 2θ.

3. The crystalline Monohydrate Form $H_A$ of the compound according to claim 1, which: (a) has an X-ray powder diffraction pattern substantially the same as the X-ray powder diffraction pattern shown in FIG. 5 when measured using CuKα radiation; or (b) has a differential scanning calorimetry (DSC) thermogram substantially the same as that shown in FIG. 6.

4. A crystalline Form A of the compound

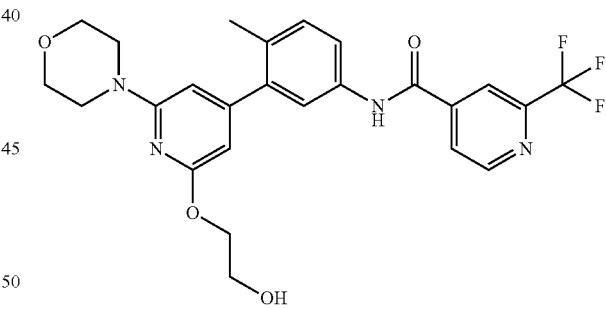

optionally in substantially pure form, wherein the compound has an X-ray powder diffraction pattern with at least four peaks having an angle of refraction 2 theta (θ) values selected from 5.8, 11.7, 14.8, 15.2, and 18.7, wherein the 2 theta (θ) values are measured using CuKα radiation and are plus or minus 0.2° 2θ.

5. The crystalline Form A of the compound according to claim 4 which has an X-ray powder diffraction pattern with at least five peaks having an angle of refraction 2 theta (θ) values selected from 5.8, 10.0, 11.7, 12.6, 13.1, 14.8, 15.2, 18.7, 20.2, and 25.1; wherein the 2 theta (θ) values are measured using CuKα radiation and are plus or minus 0.2° 2θ.

6. The crystalline Form A of the compound according to claim 4 which has an X-ray powder diffraction pattern substantially the same as the X-ray powder diffraction pattern shown in FIG. 1 when measured using CuKα radiation or which has a differential scanning calorimetry (DSC) thermogram substantially the same as that shown in FIG. 2.

7. A crystalline Form B of the compound

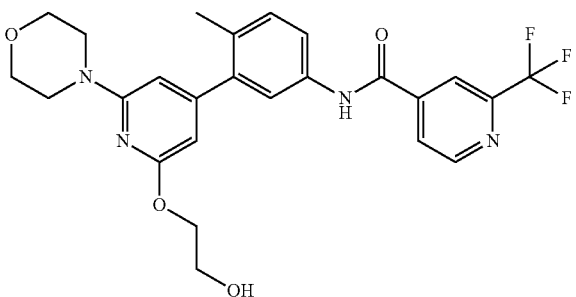 [SMILES: Cc1ccc(NC(=O)c2ccnc(C(F)(F)F)c2)cc1-c1cc(OCCO)nc(N2CCOCC2)c1]

optionally in substantially pure form, wherein the compound has an X-ray powder diffraction pattern with at least four peaks having an angle of refraction 2 theta (θ) values selected from 4.4, 13.4, 18.0, 19.5, and 23.6, wherein the 2 theta (θ) values are measured using CuKα radiation and are plus or minus 0.2° 2θ.

8. The crystalline Form B of the compound according to claim 7 which has an X-ray powder diffraction pattern with at least five peaks having an angle of refraction 2 theta (θ) values selected from 4.4, 11.3, 13.4, 18.0, 18.9, 19.5, 21.0, 21.8, 23.6, and 25.4; wherein the 2 theta (θ) values are measured using CuKα radiation and are plus or minus 0.2° 2θ.

9. The crystalline Form B of the compound according to claim 7 which has an X-ray powder diffraction pattern substantially the same as the X-ray powder diffraction pattern shown in FIG. 3 when measured using CuKα radiation; or which has a differential scanning calorimetry (DSC) thermogram substantially the same as that shown in FIG. 4.

10. A pharmaceutical composition comprising a crystalline form according to claim 1 and at least one pharmaceutically acceptable carrier or diluent.

11. A method of treating cancer, comprising administering to a subject in need thereof a therapeutically effective amount of a compound according to claim 1, wherein the cancer is selected from melanoma, non-small cell lung cancer (NSCLC), colorectal cancer (CRC), ovarian cancer, cervical cancer and pancreatic ductal adenocarcinoma (PADC).

12. The method according to claim 11, wherein the cancer expresses a MAPK mutation.

13. The method according to claim 11, wherein the cancer is characterized by at least one mutation in the B-Raf or KRAS proteins.

14. The method according to claim 11, wherein the cancer is selected from the group consisting of KRAS-and/or BRaf-mutant non-small cell lung cancer, N-RAS-mutant melanoma, KRAS-mutant ovarian cancer and KRAS-mutant pancreatic cancer.

15. The method of claim 14, wherein the pancreatic cancer is KRAS mutant pancreatic ductal adenocarcinoma.

16. A process for the preparation of the crystalline form Monohydrate $H_A$ of the compound of claim 1 comprising the steps:
(i) suspending the compound in a water miscible solvent: water mixture;
(ii) heating the mixture up to about 100° C.;
(iii) cooling the mixture to room temperature;
(iv) isolating at least a part of the crystals obtained from the mixture;
(v) optionally washing the isolated crystals; and
(vi) recovering the Monohydrate Form $H_A$.

\* \* \* \* \*